US007049088B2

(12) United States Patent
Friedman et al.

(10) Patent No.: US 7,049,088 B2
(45) Date of Patent: May 23, 2006

(54) PRMTS AS MODIFIERS OF THE P53 PATHWAY AND METHODS OF USE

(75) Inventors: Lori Friedman, San Francisco, CA (US); Gregory D. Plowman, San Carlos, CA (US); Marcia Belvin, Albany, CA (US); Helen Francis-Lang, San Francisco, CA (US); Danxi Li, San Francisco, CA (US); Roel P. Funke, South San Francisco, CA (US); Rolf Peter Ryseck, Ewing, NJ (US); Lata Jayaraman, Lawrenceville, NJ (US); David K. Bol, Gaithersburg, MD (US); Matthew Lorenzi, Philadelphia, PA (US)

(73) Assignee: Exelixis, INC, South San Francisco, CA (US)

( * ) Notice: Subject to any disclaimer, the term of this patent is extended or adjusted under 35 U.S.C. 154(b) by 0 days.

(21) Appl. No.: 10/164,278

(22) Filed: Jun. 5, 2002

(65) Prior Publication Data

Related U.S. Application Data

(60) Provisional application No. 60/296,076, filed on Jun. 5, 2001, provisional application No. 60/328,605, filed on Oct. 10, 2001, provisional application No. 60/338,733, filed on Oct. 22, 2001, provisional application No. 60/357,253, filed on Feb. 15, 2002, provisional application No. 60/357,600, filed on Feb. 15, 2002, provisional application No. 60/384,348, filed on May 30, 2002.

(51) Int. Cl.
*C12Q 1/48* (2006.01)
*C12N 9/10* (2006.01)

(52) U.S. Cl. ........................................ 435/15; 435/193

(58) Field of Classification Search .................. 435/15, 435/193

See application file for complete search history.

(56) References Cited

U.S. PATENT DOCUMENTS 6,060,250 A 5/2000 Lal et al.
6,471,959 B1 * 10/2002 Lal et al. ................... 424/94.5
6,743,614 B1 * 6/2004 Stallcup et al. ............. 435/193

FOREIGN PATENT DOCUMENTS

WO WO 03/102143 A2 * 12/2003

OTHER PUBLICATIONS

Chen et al. (Jun. 25, 1999) Science, vol. 284, pp. 2174-2177.*

Chen, D., et al., "Mus musculus protein arginine methyltransferase (Carm1) mRNA, complete cds." Genbank GI No. 5257220, Jun. 29, 1999.

NCBI Annotation Project, "*Homo sapiens* coactivator-associated arginine methyltransferase-1 (CARM1), mRNA" Genbank GI No. 18601083, May 13, 2002.

NCBI Annotation Project, "*Homo sapiens* coactivator-associated arginine methyltransferase-1 (CARM1), mRNA. " Genbank GI No. 14759767, Oct. 16, 2001.

NCBI Annotation Project, "*Homo sapiens* hypothetical protein FLJ10559 (FLJ10559), mRNA." Genbank GI No. 11422727, Oct. 16, 2001.

Frankel,A., et al., "*Homo sapiens* protein arginine N-methyltransferase 6 (PRMT6), mRNA." Genbank GI No. 8922514, Feb. 10, 2002.

NCBI Annotation Project, "*Homo sapiens* protein arginine N-methyltransferase 6 (PRMT6), mRNA." Genbank GI No. 17436208, May 8, 2002.

Strausberg,R., "*Homo sapiens*, hypothetical protein FLJ10559, clone MGC:3421 Image:3629812, mRNA, complete cds.", Genbank GI No. 12803778, Jul. 12, 2001.

Chen,D., et al., "protein arginine methyltransferase [Mus musculus]." Genbank GI No. 5257221, Jun. 28, 1999.

NCBI Annotation Project, "coactivator-associated arginine methyltransferase-1 [*Homo sapiens*]." Genbank GI No. 18601084, May 13, 2002.

NCBI Annotation Project, "coactivator-associated arginine methyltransferase-1 [*Homo sapiens*]." Genbank GI No. 14759768, Oct. 16, 2001.

NCBI Annotation Project, "hypothetical protein FLJ10559 [Homo sapiens]." Genbank GI No. 11422728, Feb. 09, 2001.

Frankel,A., et al., "hypothetical protein FLJ10559 [Homo sapiens]." Genbank GI No. 8922515, feb. 10, 2002.

Han, K. et al., S-Adenosylmethionine: Protein-Arginine N-Methyltransferase from Bovine Fetal Liver, Biochemical Archives, 1999, pp. 45-57, vol. 15.

Lin, Q. et al., Design of Allele-Specific Protein Methyltransferase inhibitors, J. Am. Chem. Soc., Nov. 28, 2001, pp. 11608-11613, vol. 123, No. 47.

Koh, S.S. et al., Synergistic Enhancement of Nuclear Receptor Function by p160 Coactivators and Two Coactivators with Protein Methyltransferase Activities, The Journal of Biological Chemistry, Jan. 12, 2001, pp. 1089-1098, vol. 276, No. 2.

* cited by examiner

*Primary Examiner*—Elizabeth Slobodyansky
(74) *Attorney, Agent, or Firm*—Laleh Shayesteh; Exelixis, INC

(57) ABSTRACT

Human PRMT genes are identified as modulators of the p53 pathway, and thus are therapeutic targets for disorders associated with defective p53 function. Methods for identifying modulators of p53, comprising screening for agents that modulate the activity of PRMT are provided.

2 Claims, No Drawings

PRMTS AS MODIFIERS OF THE P53 PATHWAY AND METHODS OF USE

REFERENCE TO RELATED APPLICATIONS

This application claims priority to U.S. provisional patent applications 60/296,076 filed Jun. 5, 2001, 60/328,605 filed Oct. 10, 2001, 60/338,733 filed Oct. 22, 2001, 60/357,253 filed Feb. 15, 2002, 60/357,600 filed Feb. 15, 2002, and 60/384,348 filed May 30, 2002.

BACKGROUND OF THE INVENTION

The p53 gene is mutated in over 50 different types of human cancers, including familial and spontaneous cancers, and is believed to be the most commonly mutated gene in human cancer (Zambetti and Levine, FASEB (1993) 7:855–865; Hollstein, et al., Nucleic Acids Res. (1994) 22:3551–3555). Greater than 90% of mutations in the p53 gene are missense mutations that alter a single amino acid that inactivates p53 function. Aberrant forms of human p53 are associated with poor prognosis, more aggressive tumors, metastasis, and short survival rates (Mitsudomi et al., Clin Cancer Res 2000 October; 6(10):4055–63; Koshland, Science (1993) 262:1953).

The human p53 protein normally functions as a central integrator of signals including DNA damage, hypoxia, nucleotide deprivation, and oncogene activation (Prives, Cell (1998) 95:5–8). In response to these signals, p53 protein levels are greatly increased with the result that the accumulated p53 activates cell cycle arrest or apoptosis depending on the nature and strength of these signals. Indeed, multiple lines of experimental evidence have pointed to a key role for p53 as a tumor suppressor (Levine, Cell (1997) 88:323–331). For example, homozygous p53 "knockout" mice are developmentally normal but exhibit nearly 100% incidence of neoplasia in the first year of life (Donehower et al., Nature (1992) 356:215–221).

The biochemical mechanisms and pathways through which p53 functions in normal and cancerous cells are not fully understood, but one clearly important aspect of p53 function is its activity as a gene-specific transcriptional activator. Among the genes with known p53-response elements are several with well-characterized roles in either regulation of the cell cycle or apoptosis, including GADD45, p21/Waf1/Cip1, cyclin G, Bax, IGF-BP3, and MDM2 (Levine, Cell (1997) 88:323–331).

The family of protein arginine N-methyltransferases (PRMTs) catalyze the sequential transfer of a methyl group from S-adenosylmethionene to the side chain nitrogens of arginine residues within proteins to form methylated arginine derivatives and S-adenosyl-L-homocysteine. The methylation of arginine residues has been implicated in the regulation of signal transduction (Altschuler L et al. (1999) J. Interferon Cytokine Res. 19:189–195; Tang J et al. (2000) J. Biol. Chem. 275:19866–19876; Bedford M. T et al. (2000) J. Biol. Chem. 275:16030–16036), transcription (Chen D et al. (1999) Science 284:2174–2177), RNA transport (McBride A E et al. (2000) J. Biol. Chem. 275:3128–3136; Yun C et al. (2000) J. Cell Biol. 150:707–718), and possibly splicing (Friesen W J et al., (2001) Mol. Cell 7:1111–1117). PRMTs are conserved in evolution (Zhang X et al. (2000) EMBO J. 19:3509–3519; Weiss V H et al. (2000) Nat. Struct. Biol. 7:1165–1171).

Coactivator associated arginine Methyltransferase 1 (CARM1/PRMT4) functions in a dual role as a protein methyltransferase and a transcriptional coactivator. CARM1 interacts with the p160 coactivators to enhance nuclear receptor transcription, enhances transcription activation by the estrogen receptor, and methylates histone H3 (Chen D et al., supra). PRMT6 is the only PRMT capable of automethylation. Of the known PRMTs, CARM1 and PRMT6 localize to the nucleus (Frankel A et al. (2002) J Biol Chem. 277:3537–3543).

The ability to manipulate the genomes of model organisms such as Drosophila provides a powerful means to analyze biochemical processes that, due to significant evolutionary conservation, has direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Mechler B M et al., 1985 EMBO J 4:1551–1557; Gateff E. 1982 Adv. Cancer Res. 37: 33–74; Watson K L., et al., 1994 J Cell Sci. 18: 19–33; Miklos G L, and Rubin G M. 1996 Cell 86:521–529; Wassarman DA, et al., 1995 Curr Opin Gen Dev 5: 44–50; and Booth D R. 1999 Cancer Metastasis Rev. 18: 261–284). For example, a genetic screen can be carried out in an invertebrate model organism having underexpression (e.g. knockout) or overexpression of a gene (referred to as a "genetic entry point") that yields a visible phenotype. Additional genes are mutated in a random or targeted manner. When a gene mutation changes the original phenotype caused by the mutation in the genetic entry point, the gene is identified as a "modifier" involved in the same or overlapping pathway as the genetic entry point. When the genetic entry point is an ortholog of a human gene implicated in a disease pathway, such as p53, modifier genes can be identified that may be attractive candidate targets for novel therapeutics.

All references cited herein, including sequence information in referenced Genbank identifier numbers and website references, are incorporated herein in their entireties.

SUMMARY OF THE INVENTION

We have discovered genes that modify the p53 pathway in Drosophila, and identified their human orthologs, hereinafter referred to as PRMT. The invention provides methods for utilizing these p53 modifier genes and polypeptides to identify PRMT-modulating agents that are candidate therapeutic agents that can be used in the treatment of disorders associated with defective or impaired p53 function and/or PRMT function. p53 function. Preferred PRMT-modulating agents specifically bind to PRMT polypeptides and restore p53 function. Other preferred PRMT-modulating agents are nucleic acid modulators such as antisense oligomers and RNAi that repress PRMT gene expression or product activity by, for example, binding to and inhibiting the respective nucleic acid (i.e. DNA or mRNA).

PRMT-modulating agents may be evaluated by any convenient in vitro or in vivo assay for molecular interaction with a PRMT polypeptide or nucleic acid. In one embodiment, candidate PRMT-modulating agents are tested with an assay system comprising a PRMT polypeptide or nucleic acid. In one preferred embodiment, the PRMT polypeptide or nucleic acid is PRMT4 (also referred to as "CARM1"). Agents that produce a change in the activity of the assay system relative to controls are identified as candidate p53 modulating agents. The assay system may be cell-based or cell-free. PRMT-modulating agents include, but are not limited to, PRMT related proteins (e.g. dominant negative mutants, and biotherapeutics); PRMT-specific antibodies; PRMT-specific antisense oligomers and other nucleic acid modulators; and chemical agents that specifically bind to or interact with PRMT (e.g. by binding to a PRMT binding partner). In one specific embodiment, a small molecule modulator is identified using a transferase assay. In specific embodiments, the screening assay system is selected from an apoptosis assay, a cell proliferation assay, an angiogenesis assay, and a hypoxic induction assay In another embodiment, candidate p53 pathway modulating agents are further tested using a second assay system that detects changes in the p53 pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the p53 pathway, such as an angiogenic, apoptotic, or cell proliferation disorder (e.g. cancer).

The invention further provides methods for modulating PRMT function and/or the p53 pathway in a mammalian cell by contacting the mammalian cell with an agent that specifically binds a PRMT polypeptide or nucleic acid. In a preferred embodiment, the PRMT polypeptide or nucleic acid is CARM1. The agent may be a small molecule modulator, a nucleic acid modulator, or an antibody and may be administered to a mammalian animal predetermined to have a pathology associated the p53 pathway.

DETAILED DESCRIPTION OF THE INVENTION

To identify modifiers of the p53 pathway in Drosophila, a genetic modifier screen was carried out in which p53 was overexpressed in the wing (Ollmann M, et al., Cell 2000 101: 91–101). The CG5358 gene was identified as a modifier of the p53 pathway. Accordingly, vertebrate orthologs of this modifier, and preferably the human orthologs, PRMT genes (i.e., nucleic acids and polypeptides) are attractive drug targets for the treatment of pathologies associated with a defective p53 signaling pathway, such as cancer.

In vitro and in vivo methods of assessing PRMT function are provided herein. Modulation of the PRMT or their respective binding partners is useful for understanding the association of the p53 pathway and its members in normal and disease conditions and for developing diagnostics and therapeutic modalities for p53 related pathologies. PRMT-modulating agents that act by inhibiting or enhancing PRMT expression, directly or indirectly, for example, by affecting a PRMT function such as enzymatic (e.g., catalytic) or binding activity, can be identified using methods provided herein. PRMT modulating agents are useful in diagnosis, therapy and pharmaceutical development.

Nucleic Acids and Polypeptides of the Invention

Sequences related to PRMT nucleic acids and polypeptides that can be used in the invention are disclosed in Genbank (referenced by Genbank identifier (GI) number) as GI#s 5257220 (SEQ ID NO:1), 18601083 (SEQ ID NO:2), 14759767 (SEQ ID NO:3), 11422727 (SEQ ID NO:4), 8922514 (SEQ ID NO:5), 17436208 (SEQ ID NO:6), and 12803778 (SEQ ID NO:7) for nucleic acid, and GI#s 5257221 (SEQ ID NO:8), 18601084 (SEQ ID NO:9), 14759768 (SEQ ID NO:10), 11422728 (SEQ ID NO: 11), and 8922515 (SEQ ID NO:12) for polypeptides. Additionally, nucleic acid sequences of SEQ ID NOs:13 and 14 and amino acid sequence of SEQ ID NO:15 can also be used in the invention.

PRMTs are transferase proteins with transferase domains. The term "PRMT polypeptide" refers to a full-length PRMT protein or a functionally active fragment or derivative thereof. A "functionally active" PRMT fragment or derivative exhibits one or more functional activities associated with a full-length, wild-type PRMT protein, such as antigenic or immunogenic activity, enzymatic activity, ability to bind natural cellular substrates, etc. The functional activity of PRMT proteins, derivatives and fragments can be assayed by various methods known to one skilled in the art (Current Protocols in Protein Science (1998) Coligan et al., eds., John Wiley & Sons, Inc., Somerset, N.J.) and as further discussed below. For purposes herein, functionally active fragments also include those fragments that comprise one or more structural domains of a PRMT, such as a transferase domain or a binding domain. Protein domains can be identified using the PFAM program (Bateman A., et al., Nucleic Acids Res, 1999, 27:260–2; http://pfam.wustl.edu). Methods for obtaining PRMT polypeptides are also further described below. In some embodiments, preferred fragments are functionally active, domain-containing fragments comprising at least 25 contiguous amino acids, preferably at least 50, more preferably 75, and most preferably at least 100 contiguous amino acids of any one of SEQ ID NOs:8, 9, 10, 11, or 12 (a PRMT). In further preferred embodiments, the fragment comprises the entire functionally active domain.

The term "PRMT nucleic acid" refers to a DNA or RNA molecule that encodes a PRMT polypeptide. Preferably, the PRMT polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with PRMT. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849–5856; Huynen M A et al., Genome Research (2000) 10:1204–1210). Programs for multiple sequence alignment, such as CLUSTAL (Thompson J D et al, 1994, Nucleic Acids Res 22:4673–4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows speciation, a single gene in one species, such as Drosophila, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403–410; http://blast.wustl.edulblast/README.html) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482–489; database: European Bioinformatics Institute http://www.ebi.ac.uk/MPsrch/; Smith and Waterman, 1981, J. of Molec.Biol., 147:195–197; Nicholas et al., 1998, "A Tutorial on Searching Sequence Databases and Sequence Scoring Methods" (www.psc.edu) and references cited therein.; W. R. Pearson, 1991, Genomics 11:635–650). This algorithm can be applied to amino acid sequences by using the scoring matrix developed by Dayhoff (Dayhoff: Atlas of Protein Sequences and Structure, M. O. Dayhoff ed., 5 suppl. 3:353–358, National Biomedical Research Foundation, Washington, D.C., USA), and normalized by Gribskov (Gribskov 1986 Nucl. Acids Res. 14(6):6745–6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of any of SEQ ID NOs:1, 2, 3, 4, 5, 6, or 7. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of any one of SEQ ID NOs:1, 2, 3, 4, 5, 6, or 7 under stringent hybridization conditions that comprise: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5× Denhardt's solution, 0.05% sodium pyrophosphate and 100 μg/ml herring sperm DNA; hybridization for 18–20 hours at 65° C. in a solution containing 6×SSC, 1× Denhardt's solution, 100 μg/ml yeast tRNA and 0.05% sodium pyrophosphate; and washing of filters at 65° C. for 1 h in a solution containing 0.2×SSC and 0.1% SDS (sodium dodecyl sulfate).

In other embodiments, moderately stringent hybridization conditions are used that comprise: pretreatment of filters containing nucleic acid for 6 h at 40° C. in a solution containing 35% formamide, 5×SSC, 50 mM Tris-HCl (pH7.5), SM EDTA, 0.1% PVP, 0.1% Ficoll, 1% BSA, and 500 μg/ml denatured salmon sperm DNA; hybridization for 18–20 h at 40° C. in a solution containing 35% formamide, 5×SSC, 50 mM Tris-HCl (pH7.5), 5 mM EDTA, 0.02% PVP, 0.02% Ficoll, 0.2% BSA, 100 μg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that comprise: incubation for 8 hours to overnight at 37° C. in a solution comprising 20% formamide, 5×SSC, 50 mM sodium phosphate (pH 7.6), 5× Denhardt's solution, 10% dextran sulfate, and 20 μg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of PRMT Nucleic Acids and Polypeptides PRMT nucleic acids and polypeptides, useful for identifying and testing agents that modulate PRMT function and for other applications related to the involvement of PRMT in the p53 pathway. PRMT nucleic acids and derivatives and orthologs thereof may be obtained using methods known to those skilled in the art. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of a PRMT protein for assays used to assess PRMT function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant PRMT is expressed in a cell line known to have defective p53 function (e.g. SAOS-2 osteoblasts, H1299 lung cancer cells, C33A and HT3 cervical cancer cells, HT-29 and DLD-1 colon cancer cells, among others, available from American Type Culture Collection (ATCC), Manassas, Va.). The recombinant cells are used in cell-based screening assay systems of the invention, as described further below.

The nucleotide sequence encoding a PRMT polypeptide can be inserted into any appropriate expression vector. The necessary transcriptional and translational signals, including promoter/enhancer element, can derive from the native PRMT gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. A host cell strain that modulates the expression of, modifies, and/or specifically processes the gene product may be used.

To detect expression of the PRMT gene product, the expression vector can comprise a promoter operably linked to a PRMT gene nucleic acid, one or more origins of replication, and, one or more selectable markers (e.g. thymidine kinase activity, resistance to antibiotics, etc.). Alternatively, recombinant expression vectors can be identified by assaying for the expression of the PRMT gene product based on the physical or functional properties of the PRMT protein in in vitro assay systems (e.g. immunoassays).

The PRMT protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105–111).

Once a recombinant cell that expresses the PRMT gene sequence is identified, the gene product can be isolated and purified using standard methods (e.g. ion exchange, affinity, and gel exclusion chromatography; centrifugation; differential solubility; electrophoresis, cite purification reference). Alternatively, native PRMT proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of PRMT or other genes associated with the p53 pathway. As used herein, mis-expression encompasses ectopic expression, overexpression, under-expression, and non-expression (e.g. by gene knock-out or blocking expression that would otherwise normally occur).

Genetically Modified Animals

Animal models that have been genetically modified to alter PRMT expression may be used in in vivo assays to test for activity of a candidate p53 modulating agent, or to further assess the role of PRMT in a p53 pathway process such as apoptosis or cell proliferation. Preferably, the altered PRMT expression results in a detectable phenotype, such as decreased or increased levels of cell proliferation, angiogenesis, or apoptosis compared to control animals having normal PRMT expression. The genetically modified animal may additionally have altered p53 expression (e.g. p53 knockout). Preferred genetically modified animals are mammals such as primates, rodents (preferably mice), cows, horses, goats, sheep, pigs, dogs and cats. Preferred non-mammalian species include zebrafish, *C. elegans*, and *Drosophila*. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761–763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438–4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No., 4,945,050, by Sandford et al.; for transgenic Drosophila see Rubin and Spradling, Science (1982) 218: 348–53 and U.S. Pat. No. 4,670,388; for transgenic insects see Berghammer A. J. et al., A Universal Marker for Transgenic Insects (1999) Nature 402:370–371; for transgenic Zebrafish see Lin S., Transgenic Zebrafish, Methods Mol Biol. (2000);136:375–3830); for microinjection procedures for fish, amphibian eggs and birds see Houdebine and Chourrout, Experientia (1991) 47:897–905; for transgenic rats see Hammer et al., Cell (1990) 63:1099–1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1197) Nature 385:810–813; and PCT International Publication Nos. WO 97/07668 and WO 97/07669).

In one embodiment, the transgenic animal is a "knock-out" animal having a heterozygous or homozygous alteration in the sequence of an endogenous PRMT gene that results in a decrease of PRMT function, preferably such that PRMT expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse PRMT gene is used to construct a homologous recombination vector suitable for altering an endogenous PRMT gene in the mouse genome. Detailed methodologies for homologous recombination in mice are available (see Capecchi, Science (1989) 244:1288–1292; Joyner et al., Nature 338:153–156). Procedures for the production of non-rodent transgenic mammals and other animals are also available (Houdebine and Chourrout, supra; Pursel et al., Science (1989) 244:1281–1288; Simms et al., Bio/Technology (1988) 6:179–183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257–264; Declerck P J et al., (1995) J Bi In another embodiment, the transgenic animal is a "knock-in" animal having an alteration in its genome that results in altered expression (e.g., increased (including ectopic) or decreased expression) of the PRMT gene, e.g., by introduction of additional copies of PRMT, or by operatively inserting a regulatory sequence that provides for altered expression of an endogenous copy of the PRMT gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232–6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of *Saccharomyces cerevisiae* (O'Gorman et al. (1991) Science 251:1351–1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83–6).

The genetically modified animals can be used in genetic studies to further elucidate the p53 pathway, as animal models of disease and disorders implicating defective p53 function, and for in vivo testing of candidate therapeutic agents, such as those identified in screens described below. The candidate therapeutic agents are administered to a genetically modified animal having altered PRMT function and phenotypic changes are compared with appropriate control animals such as genetically modified animals that receive placebo treatment, and/or animals with unaltered PRMT expression that receive candidate therapeutic agent.

In addition to the above-described genetically modified animals having altered PRMT function, animal models having defective p53 function (and otherwise normal PRMT function), can be used in the methods of the present invention. For example, a p53 knockout mouse can be used to assess, in vivo, the activity of a candidate p53 modulating agent identified in one of the in vitro assays described below. p53 knockout mice are described in the literature (Jacks et al., Nature 2001;410:1111–1116, 1043–1044; Donehower et al., supra). Preferably, the candidate p53 modulating agent when administered to a model system with cells defective in p53 function, produces a detectable phenotypic change in the model system indicating that the p53 function is restored, i.e., the cells exhibit normal cell cycle progression.

Modulating Agents

The invention provides methods to identify agents that interact with and/or modulate the function of PRMT and/or the p53 pathway. Modulating agents identified by these methods are also part of the invention. Such agents are useful in a variety of diagnostic and therapeutic applications associated with the p53 pathway, as well as in further analysis of the PRMT protein and its contribution to the p53 pathway. Accordingly, the invention also provides methods for modulating the p53 pathway comprising the step of specifically modulating PRMT activity by administering a PRMT-interacting or -modulating agent.

As used herein, a "PRMT-modulating agent" is any agent that modulates PRMT function, for example, an agent that interacts with PRMT to inhibit or enhance PRMT activity or otherwise affect normal PRMT function. PRMT function can be affected at any level, including transcription, protein expression, protein localization, and cellular or extra-cellular activity. In a preferred embodiment, the PRMT-modulating agent specifically modulates the function of the PRMT. The phrases "specific modulating agent", "specifically modulates", etc., are used herein to refer to modulating agents that directly bind to the PRMT polypeptide or nucleic acid, and preferably inhibit, enhance, or otherwise alter, the function of the PRMT. These phrases also encompass modulating agents that alter the interaction of the PRMT with a binding partner, substrate, or cofactor (e.g. by binding to a binding partner of a PRMT, or to a protein/binding partner complex, and altering PRMT function). In a further preferred embodiment, the PRMT-modulating agent is a modulator of the p53 pathway (e.g. it restores and/or up-regulates p53 function), and thus is also a "p53 modulating agent".

Preferred PRMT-modulating agents include small molecule compounds; PRMT-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., $19^{th}$ edition.

Small Molecule Modulators

Small molecules, are often preferred to modulate function of proteins with enzymatic function, and/or containing protein interaction domains. Chemical agents, referred to in the art as "small molecule" compounds are typically organic, non-peptide molecules, having a molecular weight less than 10,000, preferably less than 5,000, more preferably less than 1,000, and most preferably less than 500. This class of modulators includes chemically synthesized molecules, for instance, compounds from combinatorial chemical libraries. Synthetic compounds may be rationally designed or identified based on known or inferred properties of the PRMT protein or may be identified by screening compound libraries. Alternative appropriate modulators of this class are natural products, particularly secondary metabolites from organisms such as plants or fungi, which can also be identified by screening compound libraries for PRMT-modulating activity. Methods for generating and obtaining compounds are well known in the art (Schreiber S L, Science (2000) 151: 1964–1969; Radmann J and Gunther J, Science (2000) 151:1947–1948).

Small molecule modulators identified from screening assays, as described below, can be used as lead compounds from which candidate clinical compounds may be designed, optimized, and synthesized. Such clinical compounds may have utility in treating pathologies associated with the p53 pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific PRMT-interacting proteins are useful in a variety of diagnostic and therapeutic applications related to the p53 pathway and related disorders, as well as in validation assays for other PRMT-modulating agents. In a preferred embodiment, PRMT-interacting proteins affect normal PRMT function, including transcription, protein expression, protein localization, and cellular or extra-cellular activity. In another embodiment, PRMT-interacting proteins are useful in detecting and providing information about the function of PRMT proteins, as is relevant to p53 related disorders, such as cancer (e.g., for diagnostic means).

A PRMT-interacting protein may be endogenous, i.e. one that naturally interacts genetically or biochemically with a PRMT, such as a member of the PRMT pathway that modulates PRMT expression, localization, and/or activity. PRMT-modulators include dominant negative forms of PRMT-interacting proteins and of PRMT proteins themselves. Yeast two-hybrid and variant screens offer preferred methods for identifying endogenous PRMT-interacting proteins (Finley, R. L. et al. (1996) in DNA Cloning-Expression Systems: A Practical Approach, eds. Glover D. & Hames B. D (Oxford University Press, Oxford, England), pp. 169–203; Fashema S F et al., Gene 250:1–14; Drees B L Curr Opin Chem Biol (1999) 3:64–70; Vidal M and Legrain P Nucleic Acids Res (1999) 27:919–29; and U.S. Pat. No. 5,928,868). Mass spectrometry is an alternative preferred method for the elucidation of protein complexes (reviewed in, e.g., Pandley A and Mann M, Nature (2000) 405:837–846; Yates JR 3$^{rd}$, Trends Genet (2000) 16:5–8).

An PRMT-interacting protein may be an exogenous protein, such as a PRMT-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). PRMT antibodies are further discussed below.

In preferred embodiments, a PRMT-interacting protein specifically binds a PRMT protein. In alternative preferred embodiments, a PRMT-modulating agent binds a PRMT substrate, binding partner, or cofactor.

Antibodies

In another embodiment, the protein modulator is a PRMT specific antibody agonist or antagonist. The antibodies have therapeutic and diagnostic utilities, and can be used in screening assays to identify PRMT modulators. The antibodies can also be used in dissecting the portions of the PRMT pathway responsible for various cellular responses and in the general processing and maturation of the PRMT.

Antibodies that specifically bind PRMT polypeptides can be generated using known methods. Preferably the antibody is specific to a mammalian ortholog of PRMT polypeptide, and more preferably, to human PRMT. Antibodies may be polyclonal, monoclonal (mAbs), humanized or chimeric antibodies, single chain antibodies, Fab fragments, F(ab') .sub.2 fragments, fragments produced by a FAb expression library, anti-idiotypic (anti-Id) antibodies, and epitope-binding fragments of any of the above. Epitopes of PRMT which are particularly antigenic can be selected, for example, by routine screening of PRMT polypeptides for antigenicity or by applying a theoretical method for selecting antigenic regions of a protein (Hopp and Wood (1981), Proc. Natl. Acad. Sci. U.S.A. 78:3824–28; Hopp and Wood, (1983) Mol. Immunol. 20:483–89; Sutcliffe et al., (1983) Science 219:660–66) to the amino acid sequence shown in any of SEQ ID NOs:8, 9, 10, 11, or 12. Monoclonal antibodies with affinities of $10^8$ $M^{-1}$ preferably $10^9$ $M^{-1}$ to $10^{10}$ $M^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of PRMT or substantially purified fragments thereof. If PRMT fragments are used, they preferably comprise at least 10, and more preferably, at least 20 contiguous amino acids of a PRMT protein. In a particular embodiment, PRMT-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of PRMT-specific antibodies is assayed by an appropriate assay such as a solid phase enzyme-linked immunosorbant assay (ELISA) using immobilized corresponding PRMT polypeptides. Other assays, such as radioimmunoassays or fluorescent assays might also be used.

Chimeric antibodies specific to PRMT polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851–6855; Neuberger et al., Nature (1984) 312:604–608; Takeda et al., Nature (1985) 31:452–454). Humanized antibodies, which are a form of chimeric antibodies, can be generated by grafting complementary-determining regions (CDRs) (Carlos, T. M., J. M. Harlan. 1994. Blood 84:2068–2101) of mouse antibodies into a background of human framework regions and constant regions by recombinant DNA technology (Riechmann L M, et al., 1988 Nature 323: 323–327). Humanized antibodies contain ~10% murine sequences and ~90% human sequences, and thus further reduce or eliminate immunogenicity, while retaining the antibody specificities (Co M S, and Queen C. 1991 Nature 351: 501–501; Morrison S L. 1992 Ann. Rev. Immun. 10:239–265). Humanized antibodies and methods of their production are well-known in the art (U.S. Pat. Nos. 5,530,101, 5,585,089, 5,693,762, and 6,180,370).

PRMT-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423–426; Huston et al., Proc. Natl. Acad. Sci. USA (1988) 85:5879–5883; and Ward et al., Nature (1989) 334: 544–546).

Other suitable techniques for antibody production involve in vitro exposure of lymphocytes to the antigenic polypeptides or alternatively to selection of libraries of antibodies in phage or similar vectors (Huse et al., Science (1989) 246: 1275–1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131–134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816,567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg-to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859,206; WO0073469).

Nucleic Acid Modulators

Other preferred PRMT-modulating agents comprise nucleic acid molecules, such as antisense oligomers or double stranded RNA (dsRNA), which generally inhibit PRMT activity. Preferred nucleic acid modulators interfere with the function of the PRMT nucleic acid such as DNA replication, transcription, translocation of the PRMT RNA to the site of protein translation, translation of protein from the PRMT RNA, splicing of the PRMT RNA to yield one or more mRNA species, or catalytic activity which may be engaged in or facilitated by the PRMT RNA.

In one embodiment, the antisense oligomer is an oligonucleotide that is sufficiently complementary to a PRMT mRNA to bind to and prevent translation, preferably by binding to the 5' untranslated region. PRMT-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphodiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000) 22(3):271–281; Summerton J, and Weller D. 1997 Antisense Nucleic Acid Drug Dev.:7:187–95; U.S. Pat. No. 5,235,033; and U.S. Pat No. 5,378,841).

Alternative preferred PRMT nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in *C. elegans*, Drosophila, plants, and humans are known in the art (Fire A, et al., 1998 Nature 391:806–811; Fire, A. Trends Genet. 15, 358–363 (1999); Sharp, P. A. RNA interference 2001. Genes Dev. 15, 485490 (2001); Hammond, S. M., et al., Nature Rev. Genet. 2, 110–1119 (2001); Tuschl, T. Chem. Biochem. 2, 239–245 (2001); Hamilton, A. et al., Science 286, 950–952 (1999); Hammond, S. M., et al., Nature 404, 293–296 (2000); Zamore, P. D., et al., Cell 101, 25–33 (2000); Bernstein, E., et al., Nature 409, 363–366 (2001); Elbashir, S. M., et al., Genes Dev. 15, 188–200 (2001); WO0129058; WO9932619; Elbashir S M, et al., 2001 Nature 411:494–498).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923–1937; Tonkinson J L et al., Antisense Oligodeoxynucleotides as Clinical Therapeutic Agents, Cancer Invest. (1996) 14:54–65). Accordingly, in one aspect of the invention, a PRMT-specific nucleic acid modulator is used in an assay to further elucidate the role of the PRMT in the p53 pathway, and/or its relationship to other members of the pathway. In another aspect of the invention, a PRMT-specific antisense oligomer is used as a therapeutic agent for treatment of p53-related disease states.

Assay Systems

The invention provides assay systems and screening methods for identifying specific modulators of PRMT activity. As used herein, an "assay system" encompasses all the components required for performing and analyzing results of an assay that detects and/or measures a particular event. In general, primary assays are used to identify or confirm a modulator's specific biochemical or molecular effect with respect to the PRMT nucleic acid or protein. In general, secondary assays further assess the activity of a PRMT modulating agent identified by a primary assay and may confirm that the modulating agent affects PRMT in a manner relevant to the p53 pathway. In some cases, PRMT modulators will be directly tested in a secondary assay.

In a preferred embodiment, the screening method comprises contacting a suitable assay system comprising a PRMT polypeptide with a candidate agent under conditions whereby, but for the presence of the agent, the system provides a reference activity (e.g. transferase activity), which is based on the particular molecular event the screening method detects. A statistically significant difference between the agent-biased activity and the reference activity indicates that the candidate agent modulates PRMT activity, and hence the p53 pathway. The PRMT polypeptide or nucleic acid used in the assay may comprise any of the nucleic acids or polypeptides described above (e.g. SEQ ID NOs 1–15). In one preferred embodiment, the PRMT is a CARM1, comprising a nucleic acid sequence selected from any one of SEQ ID NOs 1–3, 13 and 14, or an amino acid sequence selected from any one of SEQ ID NOs 8–10, and 15. In a further preferred embodiment, the CARM1 nucleic acid comprises SEQ ID NO:13 or 14, and the protein comprises SEQ ID NO:9, 10 or 15.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384–91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicty and changes in cellular morphology or other cellular characteristics. Appropriate screening assays may use a wide range of detection methods including fluorescent, radioactive, calorimetric, spectrophotometric, and amperometric methods, to provide a read-out for the particular molecular event detected.

Cell-based screening assays usually require systems for recombinant expression of PRMT and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when PRMT-interacting proteins are used in screens to identify small molecule modulators, the binding specificity of the interacting protein to the PRMT protein may be assayed by various known methods such as substrate processing (e.g. ability of the candidate PRMT-specific binding agents to function as negative effectors in PRMT-expressing cells), binding equilibrium constants (usually at least about $10^7$ $M^{-1}$, preferably at least about $10^8$ $M^{-1}$, more preferably at least about $10^9$ $M^{-1}$), and immunogenicity (e.g. ability to elicit PRMT specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a PRMT polypeptide, a fusion protein thereof, or to cells or membranes bearing the polypeptide or fusion protein. The PRMT polypeptide can be full length or a fragment thereof that retains functional PRMT activity. The PRMT polypeptide may be fused to another polypeptide, such as a peptide tag for detection or anchoring, or to another tag. The PRMT polypeptide is preferably human PRMT, or is an ortholog or derivative thereof as described above. In a preferred embodiment, the screening assay detects candidate agent-based modulation of PRMT interaction with a binding target, such as an endogenous or exogenous protein or other substrate that has PRMT—specific binding activity, and can be used to assess normal PRMT gene function.

Suitable assay formats that may be adapted to screen for PRMT modulators are known in the art. Preferred screening assays are high throughput or ultra high throughput and thus provide automated, cost-effective means of screening compound libraries for lead compounds (Fernandes P B, Curr Opin Chem Biol (1998) 2:597–603; Sundberg S A, Curr Opin Biotechnol 2000, 11:47–53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730–4; Fernandes P B, supra; Hertzberg R P and Pope A J, Curr Opin Chem Biol (2000) 4:445–451).

A variety of suitable assay systems may be used to identify candidate PRMT and p53 pathway modulators (e.g. U.S. Pat. No. 6,020,135 (p53 modulation)). Specific preferred assays are described in more detail below.

Transferase assays. Methyltransferase assays are well known in the art, and may be performed as described (Tang J et al. (2000) J Biol Chem. 275:7723–7730). Briefly, hypomethylated cell lysates are produced, and the ability of endogenous methyltransferases present in the hypomethylated cell lysate to methylate various substrates after addition of [$^3$H] S-adenosylmethionene is evaluated.

Apoptosis assays. Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730–41). An apoptosis assay system may comprise a cell that expresses a PRMT, and that optionally has defective p53 function (e.g. p53 is over-expressed or under-expressed relative to wild-type cells). A test agent can be added to the apoptosis assay system and changes in induction of apoptosis relative to controls where no test agent is added, identify candidate p53 modulating agents. In some embodiments of the invention, an apoptosis assay may be used as a secondary assay to test a candidate p53 modulating agents that is initially identified using a cell-free assay system. An apoptosis assay may also be used to test whether PRMT function plays a direct role in apoptosis. For example, an apoptosis assay may be performed on cells that over- or under-express PRMT relative to wild type cells. Differences in apoptotic response compared to wild type cells suggests that the PRMT plays a direct role in the apoptotic response. Apoptosis assays are described further in U.S. Pat. No. 6,133,437.

Cell proliferation and cell cycle assays. Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell Proliferation may also be examined using $[^3H]$-thymidine incorporation (Chen, J., 1996, Oncogene 13:1395–403; Jeoung, J., 1995, J. Biol. Chem. 270:18367–73). This assay allows for quantitative characterization of S-phase DNA syntheses. In this assay, cells synthesizing DNA will incorporate $[^3H]$-thymidine into newly synthesized DNA. Incorporation can then be measured by standard techniques such as by counting of radioisotope in a scintillation counter (e.g., Beckman LS 3800 Liquid Scintillation Counter).

Cell proliferation may also be assayed by colony formation in soft agar (Sambrook et al., Molecular Cloning, Cold Spring Harbor (1989)). For example, cells transformed with PRMT are seeded in soft agar plates, and colonies are measured and counted after two weeks incubation.

Involvement of a gene in the cell cycle may be assayed by flow cytometry (Gray J W et al. (1986) Int J Radiat Biol Relat Stud Phys Chem Med 49:237–55). Cells transfected with a PRMT may be stained with propidium iodide and evaluated in a flow cytometer (available from Becton Dickinson).

Accordingly, a cell proliferation or cell cycle assay system may comprise a cell that expresses a PRMT, and that optionally has defective p53 function (e.g. p53 is over-expressed or under-expressed relative to wild-type cells). A test agent can be added to the assay system and changes in cell proliferation or cell cycle relative to controls where no test agent is added, identify candidate p53 modulating agents. In some embodiments of the invention, the cell proliferation or cell cycle assay may be used as a secondary assay to test a candidate $p^{53}$ modulating agents that is initially identified using another assay system such as a cell-free assay system. A cell proliferation assay may also be used to test whether PRMT function plays a direct role in cell proliferation or cell cycle. For example, a cell proliferation or cell cycle assay may be performed on cells that over- or under-express PRMT relative to wild type cells. Differences in proliferation or cell cycle compared to wild type cells suggests that the PRMT plays a direct role in cell proliferation or cell cycle.

Angiogenesis. Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on Matrigel® (Becton Dickinson). Accordingly, an angiogenesis assay system may comprise a cell that expresses a PRMT, and that optionally has defective p53 function (e.g. p53 is over-expressed or under-expressed relative to wild-type cells). A test agent can be added to the angiogenesis assay system and changes in angiogenesis relative to controls where no test agent is added, identify candidate p53 modulating agents. In some embodiments of the invention, the angiogenesis assay may be used as a secondary assay to test a candidate p53 modulating agents that is initially identified using another assay system. An angiogenesis assay may also be used to test whether PRMT function plays a direct role in cell proliferation. For example, an angiogenesis assay may be performed on cells that over- or under-express PRMT relative to wild type cells. Differences in angiogenesis compared to wild type cells suggests that the PRMT plays a direct role in angiogenesis.

Hypoxic induction. The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glyolytic enzymes and VEGF. Induction of such genes by hypoxic conditions may be assayed by growing cells transfected with PRMT in hypoxic conditions (such as with 0.1% O2, 5% CO2, and balance N2, generated in a Napco 7001 incubator (Precision Scientific)) and normoxic conditions, followed by assessment of gene activity or expression by Taqman®. For example, a hypoxic induction assay system may comprise a cell that expresses a PRMT, and that optionally has a mutated p53 (e.g. p53 is over-expressed or under-expressed relative to wild-type cells). A test agent can be added to the hypoxic induction assay system and changes in hypoxic response relative to controls where no test agent is added, identify candidate p53 modulating agents. In some embodiments of the invention, the hypoxic induction assay may be used as a secondary assay to test a candidate p53 modulating agents that is initially identified using another assay system. A hypoxic induction assay may also be used to test whether PRMT function plays a direct role in the hypoxic response. For example, a hypoxic induction assay may be performed on cells that over- or under-express PRMT relative to wild type cells. Differences in hypoxic response compared to wild type cells suggests that the PRMT plays a direct role in hypoxic induction.

Cell adhesion. Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12(3):346–53).

Primary Assays for Antibody Modulators

For antibody modulators, appropriate primary assays test is a binding assay that tests the antibody's affinity to and specificity for the PRMT protein. Methods for testing antibody affinity and specificity are well known in the art (Harlow and Lane, 1988, 1999, supra). The enzyme-linked immunosorbant assay (ELISA) is a preferred method for detecting PRMT-specific antibodies; others include FACS assays, radioimmunoassays, and fluorescent assays.

Primary Assays for Nucleic Acid Modulators

For nucleic acid modulators, primary assays may test the ability of the nucleic acid modulator to inhibit or enhance PRMT gene expression, preferably mRNA expression. In general, expression analysis comprises comparing PRMT expression in like populations of cells (e.g., two pools of cells that endogenously or recombinantly express PRMT) in the presence and absence of the nucleic acid modulator. Methods for analyzing mRNA and protein expression are well known in the art. For instance, Northern blotting, slot blotting, ribonuclease protection, quantitative RT-PCR (e.g., using the TaqMan®, PE Applied Biosystems), or microarray analysis may be used to confirm that PRMT mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112–125; Kallioniemi O P, Ann Med 2001, 33:142–147; Blohm D H and Guiseppi-Elie, A Curr Opin Biotechnol 2001, 12:41–47). Protein expression may also be monitored. Proteins are most commonly detected with specific antibodies or antisera directed against either the PRMT protein or specific peptides. A variety of means including Western blotting, ELISA, or in situ detection, are available (Harlow E and Lane D, 1988 and 1999, supra).

Secondary Assays

Secondary assays may be used to further assess the activity of PRMT-modulating agent identified by any of the above methods to confirm that the modulating agent affects PRMT in a manner relevant to the p53 pathway. As used herein, PRMT-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with PRMT.

Secondary assays generally compare like populations of cells or animals (e.g., two pools of cells or animals that endogenously or recombinantly express PRMT) in the presence and absence of the candidate modulator. In general, such assays test whether treatment of cells or animals with a candidate PRMT-modulating agent results in changes in the p53 pathway in comparison to untreated (or mock- or placebo-treated) cells or animals. Certain assays use "sensitized genetic backgrounds", which, as used herein, describe cells or animals engineered for altered expression of genes in the p53 or interacting pathways.

Cell-Based Assays

Cell based assays may use a variety of mammalian cell lines known to have defective p53 function (e.g. SAOS-2 osteoblasts, H1299 lung cancer cells, C33A and HT3 cervical cancer cells, HT-29 and DLD-1 colon cancer cells, among others, available from American Type Culture Collection (ATCC), Manassas, Va.). Cell based assays may detect endogenous p53 pathway activity or may rely on recombinant expression of p53 pathway components. Any of the aforementioned assays may be used in this cell-based format. Candidate modulators are typically added to the cell media but may also be injected into cells or delivered by any other efficacious means.

Animal Assays

A variety of non-human animal models of normal or defective p53 pathway may be used to test candidate PRMT modulators. Models for defective p53 pathway typically use genetically modified animals that have been engineered to mis-express (e.g., over-express or lack expression in) genes involved in the p53 pathway. Assays generally require systemic delivery of the candidate modulators, such as by oral administration, injection, etc.

In a preferred embodiment, p53 pathway activity is assessed by monitoring neovascularization and angiogenesis. Animal models with defective and normal p53 are used to test the candidate modulator's affect on PRMT in Matrigel® assays. Matrigel® is an extract of basement membrane proteins, and is composed primarily of laminin, collagen IV, and heparin sulfate proteoglycan. It is provided as a sterile liquid at 4° C., but rapidly forms a solid gel at 37° C. Liquid Matrigel® is mixed with various angiogenic agents, such as bFGF and VEGF, or with human tumor cells which over-express the PRMT. The mixture is then injected subcutaneously (SC) into female athymic nude mice (Taconic, Germantown, N.Y.) to support an intense vascular response. Mice with Matrigel® pellets may be dosed via oral (PO), intraperitoneal (IP), or intravenous (IV) routes with the candidate modulator. Mice are euthanized 5–12 days post-injection, and the Matrigel® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on PRMT is assessed via tumorigenicity assays. In one example, xenograft human tumors are implanted SC into female athymic mice, 6–7 week old, as single cell suspensions either from a pre-existing tumor or from in vitro culture. The tumors which express the PRMT endogenously are injected in the flank, $1\times10^5$ to $1\times10^7$ cells per mouse in a volume of 100 μL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

Diagnostic and Therapeutic Uses

Specific PRMT-modulating agents are useful in a variety of diagnostic and therapeutic applications where disease or disease prognosis is related to defects in the p53 pathway, such as angiogenic, apoptotic, or cell proliferation disorders. Accordingly, t h e invention also provides methods for modulating the p53 pathway in a cell, preferably a cell pre-determined to have defective or impaired p53 function (e.g. due to overexpression, underexpression, or misexpression of p53, or due to gene mutations), comprising the step of administering an agent to the cell that specifically modulates PRMT activity. Preferably, the modulating agent produces a detectable phenotypic change in the cell indicating that the p53 function is restored. The phrase "function is restored", and equivalents, as used herein, means that the desired phenotype is achieved, or is brought closer to normal compared to untreated cells. For example, with restored p53 function, cell proliferation and/or progression through cell cycle may normalize, or be brought closer to normal relative to untreated cells. The invention also provides methods for treating disorders or disease associated with impaired p53 function by administering a therapeutically effective amount of a PRMT-modulating agent that modulates the p53 pathway. The invention further provides methods for modulating PRMT function in a cell, preferably a cell pre-determined to have defective or impaired PRMT function, by administering a PRMT-modulating agent. Additionally, the invention provides a method for treating disorders or disease associated with impaired PRMT function by administering a therapeutically effective amount of a PRMT-modulating agent. In certain embodiments the impaired PRMT function is attributable to impaired CARM1.

The discovery that PRMT is implicated in p53 pathway provides for a variety of methods that can be employed for the diagnostic and prognostic evaluation of diseases and disorders involving defects in the p53 pathway and for the identification of subjects having a predisposition to such diseases and disorders.

Various expression analysis methods can be used to diagnose whether PRMT expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112–125; Kallioniemi O P, Ann Med 2001, 33:142–147; Blohm and Guiseppi-Elie, Curr Opin Biotechnol 2001, 12:41–47). Tissues having a disease or disorder implicating defective p53 signaling that express a PRMT, are identified as amenable to treatment with a PRMT modulating agent. In a preferred application, the p53 defective tissue overexpresses a PRMT relative to normal tissue. For example, a Northern blot analysis of mRNA from tumor and normal cell lines, or from tumor and matching normal tissue samples from the same patient, using full or partial PRMT cDNA sequences as probes, can determine whether particular tumors express or overexpress PRMT. Alternatively, the TaqMan® is used for quantitative RT-PCR analysis of PRMT expression in cell lines, normal tissues and tumor samples (PE Applied Biosystems).

Various other diagnostic methods may be performed, for example, utilizing reagents such as the PRMT oligonucleotides, and antibodies directed against a PRMT, as described above for: (1) the detection of the presence of PRMT gene mutations, or the detection of either over- or under-expression of PRMT MRNA relative to the non-disorder state; (2) the detection of either an over- or an under-abundance of PRMT gene product relative to the non-disorder state; and (3) the detection of perturbations or abnormalities in the signal transduction pathway mediated by PRMT.

Thus, in a specific embodiment, the invention is drawn to a method for diagnosing a disease or disorder in a patient that is associated with alterations in PRMT expression, the method comprising: a) obtaining a biological sample from the patient; b) contacting the sample with a probe for PRMT expression; c) comparing results from step (b) with a control; and d) determining whether step (c) indicates a likelihood of the disease or disorder. Preferably, the disease is cancer, most preferably a cancer selected from the group consisting of colon cancer, lung cancer, breast cancer, and ovarian cancer. The probe may be either DNA or protein, including an antibody.

EXAMPLES

The following experimental section and examples are offered by way of illustration and not by way of limitation.

I. Drosophila p53 Screen

The Drosophila p53 gene was overexpressed specifically in the wing using the vestigial margin quadrant enhancer. Increasing quantities of Drosophila p53 (titrated using different strength transgenic inserts in 1 or 2 copies) caused deterioration of normal wing morphology from mild to strong, with phenotypes including disruption of pattern and polarity of wing hairs, shortening and thickening of wing veins, progressive crumpling of the wing and appearance of dark "death" inclusions in wing blade. In a screen designed to identify enhancers and suppressors of Drosophila p53, homozygous females carrying two copies of p53 were crossed to 5663 males carrying random insertions of a piggyBac transposon (Fraser M et al., Virology (1985) 145:356–361). Progeny containing insertions were compared to non-insertion-bearing sibling progeny for enhancement or suppression of the p53 phenotypes. Sequence information surrounding the piggyBac insertion site was used to identify the modifier genes. Modifiers of the wing phenotype were identified as members of the p53 pathway. CG5358 was an enhancer of the wing phenotype. Human orthologs of the modifiers are referred to herein as PRMT.

BLAST analysis (Altschul et al., supra) was employed to identify Targets from Drosophila modifiers. For example, amino acid sequence of CG5358 from drosophila shares 59% and 38% sequence identity with SEQ ID NOs:9 and 12, respectively.

Various domains, signals, and functional subunits in proteins were analyzed using the PSORT (Nakai K., and Horton P., Trends Biochem Sci, 1999, 24:34–6; Kenta Nakai, Protein sorting signals and prediction of subcellular localization, Adv. Protein Chem. 54, 277–344 (2000)), PFAM (Bateman A., et al., Nucleic Acids Res, 1999, 27:260–2; http://pfam.wustl.edu), SMART (Ponting C P, et al., SMART: identification and annotation of domains from signaling and extracellular protein sequences. Nucleic Acids Res. 1999 Jan 1;27(1):229–32), TM-HMM (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175–182 Ed J. Glasgow, T. Littlejohn, F. Major, R. Lathrop, D. Sankoff, and C. Sensen Menlo Park, Calif.: AAAI Press, 1998), and dust (Remm M, and Sonnhammer E. Classification of transmembrane protein families in the *Caenorhabditis elegans* genome and identification of human orthologs. Genome Res. 2000 November;10(11):1679–89) programs.

II. Expression analysis

All cell lines used in the following experiments are NCI (National Cancer Institute) lines, and are available from ATCC (American Type Culture Collection, Manassas, Va. 20110–2209). Normal and tumor tissues were obtained from Impath, U C Davis, Clontech, Stratagene, and Ambion.

TaqMan analysis was used to assess expression levels of the disclosed genes in various samples.

RNA was extracted from each tissue sample using Qiagen (Valencia, Calif.) RNeasy kits, following manufacturer's protocols, to a final concentration of 50 ng/μl. Single stranded cDNA was then synthesized by reverse transcribing the RNA samples using random hexamers and 500 ng of total RNA per reaction, following protocol 4304965 of Applied Biosystems (Foster City, Calif., http://www.appliedbiosystems.com/).

Primers for expression analysis using TaqMan assay (Applied Biosystems, Foster City, Calif.) were prepared according to the TaqMan protocols, and the following criteria: a) primer pairs were designed to span introns to eliminate genomic contamination, and b) each primer pair produced only one product.

Taqman reactions were carried out following manufacturer's protocols, in 25 μl total volume for 96-well plates and 10 μl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor—average(all normal samples) >2×STDEV (all normal samples)).

GI#14759767 (SEQ ID NO:3) was overexpressed in 8/30 matched colon tumors, 7/13 matched lung tumors, and 3/7 matched ovarian tumors. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

In further expression analysis studies, human CARM1 (SEQ ID NO: 14) message levels in a wide variety of well-characterized tumor cell-lines were analyzed using Taqman. Results showed that hCARM-1 was significantly upregulated in lung and colon tumor derived cell-lines and to a lesser extent in breast and ovarian cell lines. In another assay, CARM-1 protein (SEQ ID NO:9) levels in multiple tumor biopsy samples from lung and colon cancer patients and their adjacent normal tissue counterparts were stained with an anti-CARM-1 specific antibody. The results showed elevated CARM-I levels in many tumor-derived tissues but not in the corresponding normal tissue.

III. Methylation Assay

In order to evaluate whether the full-length hCARM-1 had methylating activity we performed a methylation reaction. Mouse CARM-1 (SEQ ID NO: 8) has been previously shown to specifically methylate Histone H3 in vitro and in vivo. We asked whether our human homolog was also capable of exhibiting the same substrate preference. hCARM-1 (SEQ ID NO:9) was produced in and purified from baculovirus infected insect cells and increasing amounts of the purified enzyme were added to reactions containing a constant amount of recombinant Histone H3. Our experiments showed that hCARM-1 methylates Histone H3 efficiently. Interestingly, a previously documented general methylation inhibitor, homocysteine, effectively inhibited hCARM-I mediated methylation.

Methylation activity assay: Reactions were performed in 1X methylation buffer containing 20 mM Tris.HCl, pH 8.0, 200 mM NaCl and 0.4 mM EDTA. Reactions were assembled with 2.5 μg of Histone H3 and increasing amounts of hCARM-1 (0.25 μg, 0.5 μg, 1 25 μg, 2.5 μg, 3.75 μg, 5 μg, or 7.5 μg). A mock reaction where hCARM-I (SEQ ID NO:14) was omitted was used as the negative control. Reactions were incubated at 30° C. for 1 hr. prior to loading on a 10–20% gradient SDS-PAGE. The gel was fixed, dried, and exposed to film.

IV. Cell-Based Assays

Mouse CARM-1 has been implicated as a co-activator of the androgen and estrogen receptor mediated signaling pathways along with the well-known steroid co-activator GRIP-I. We were therefore interested in testing the contribution, if any, of our human clone to these pathways. When full-length hCARM-I (SEQ ID NO:14) was co-transfected with GRIP-1 and the estrogen receptor (ER) into the breast cancer cell line T47D, we obtained a clear hCARM-1 (SEQ ID NO:14) concentration-dependent increase in the estradiol mediated induction of a reporter construct containing an ER dependent promoter in front of the luciferase gene, when compared to the induction obtained with GRIP-1 and ER alone. Conversely, co-transfection of antisense oligos to hCARM-1 (SEQ ID NO: 14) effectively abrogated activation of the ER dependent reporter in the presence of transfected hCARM-1 (SEQ ID NO:14).

Interestingly, a similar inhibitory effect on ER dependent activation could be obtained by transfection of CARM-1 antisense oligos even in the absence of any exogenous (transfected) proteins. Thus, antagonizing endogenous CARM-1 is deleterious to hormone dependent activation by endogeous ER. Similar results were obtained upon cotransfection of hCARM-1 (SEQ ID NO:14) antisense oligos into MDA-MB-453 breast cancer cells to assess andogen receptor (AR) dependent signaling. Our results therefore implicate an essential role for hCARM-1 in AR and ER mediated signaling in cells.

Transfection assays: Cells were plated in 12-well dishes and allowed to adhere and grow overnight to 80% confluency at the time of transfection. Tranfections were perfomed in triplicate using Lipofectamine 2000 (Gibco) and Opti-MEM media. Total amount of DNA transfected was held constant within experiments. Six hrs. post transfection the Lipofectamine-DNA mix was removed and replaced with fresh media containing 10% serum. Hormone (dihydrotestosterone or estradiol) was added at this time and reporter activation measured after 24 hr.

V. High-Throughput In Vitro Fluorescence Polarization Assay

Fluorescently-labeled PRMT peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of PRMT activity.

VI. High-Throughput In Vitro Binding Assay.

$^{33}$P-labeled PRMT peptide is added in an assay buffer (100 mM KCl, 20 mM HEPES pH 7.6, 1 mM $MgCl_2$, 1% glycerol, 0.5% NP-40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate p53 modulating agents.

VII. Immunoprecipitations and Immunoblotting

For coprecipitation of transfected proteins, $3\times10^6$ appropriate recombinant cells containing the PRMT proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 µl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

What is claimed is:

1. A method of identifying a protein arginine methyltransferase (PRMT)-modulating agent, said method comprising the steps of:

(a) providing a purified or recombinant PRMT polypeptide comprising the amino acid sequence as set forth in SEQ ID NO:15;

(b) contacting the PRMT polypeptide with a test agent under conditions suitable for the PRMT activity of the PRMT polypeptide; and (c) detecting the PRMT activity of the PRMT polypeptide, wherein a difference between the PRMT activity in the presence and absence the test agent identifies the test agent as a PRMT-modulating agent.

2. The method of claim 1 wherein the test agent is an organic, non-peptide molecule, having a molecular weight less than 1,000 daltons.

* * * * *

SEQUENCE LISTING

<160> NUMBER OF SEQ ID NOS: 15

<210> SEQ ID NO 1
<211> LENGTH: 3124
<212> TYPE: DNA
<213> ORGANISM: Mus musculus

<400> SEQUENCE: 1
agggggcctg gagccggacc taagatggca gcggcggcag cgacggcggt ggggccgggt 60
gcggggagcg ctggggtggc gggcccgggc ggcgcggggc cctgcgctac agtgtctgtg 120
ttcccgggcg cccgcctcct cactatcggc gacgcgaacg gcgagatcca gcggcacgcg 180
gagcagcagg cgctgcgcct tgaggtgcgc gccggaccag acgcggcggg catcgccctc 240
tacagccatg aagatgtgtg tgttttcaag tgctcggtgt cccgagagac agagtgcagt 300
cgtgtgggca gacagtcctt catcatcacc ctgggctgca acagcgtcct catccagttt 360
gccacacccc acgatttctg ttctttctac aacatcctga aaacctgtcg gggccacaca 420
ctggagcgct ctgtgttcag tgagcggaca gaggaatcct cagctgtgca gtacttccag 480
ttctatggct acctatccca gcagcagaac atgatgcagg actatgtgcg gacaggcacc 540
taccagcgtg cgatcctgca gaaccacacg gacttcaagg acaagatcgt tctagatgtg 600
ggctgtggct ctgggatcct gtcatttttt gctgctcaag caggagccag gaaaatttat 660
gcagtggaag ccagcaccat ggctcagcat gcagaggtcc tggtgaagag taacaatctg 720
acagaccgca tcgtggtcat ccctggcaaa gtagaggagg tctcattgcc tgagcaagtg 780
gacattatca tctcagagcc catgggctac atgctcttca atgaacgaat gctcgagagc 840

-continued

```
tacctccatg ccaaaaagta cctgaagcct agtggaaaca tgttccccac cattggtgat    900
gtccacctcg cacccttcac tgatgaacag ctctacatgg agcagttcac caaagccaac    960
ttccggtacc agccatcctt ccatggagtg gacctgtcgg ccctcagagg tgccgctgtg   1020
gatgagtact tccggcaacc tgtggtggac acatttgaca tccggatcct gatggccaaa   1080
tctgtcaagt acacagtgaa cttcttagaa gccaaagaag gcgatttgca caggatagaa   1140
atcccattca aattccacat gctgcattca gggctagtcc atggcttggc cttctggttc   1200
gatgttgctt tcattggctc cataatgacc gtgtggctat ccacagcccc aacagagccc   1260
ctgacccact ggtaccaggt ccggtgcctc ttccagtcac cgttgtttgc caaggccggg   1320
gacacgctct cagggacatg tctgcttatt gccaacaaaa gacagagcta tgacatcagt   1380
attgtggcac aggtggacca gacaggctcc aagtccagta acctgctgga tctaaagaac   1440
cccttcttca ggtacacagg tacaacccca tcacccccac ctggctcaca ctacacgtct   1500
ccctcggaga atatgtggaa cacaggaagc acctataatc tcagcagcgg ggtggctgtg   1560
gctggaatgc ctactgccta cgacctgagc agtgttattg ccggcggctc cagtgtgggt   1620
cacaacaacc tgattccctt agctaacaca gggattgtca atcacaccca ctcccggatg   1680
ggctccataa tgagcacggg cattgtccaa ggctcctcag gtgcccaggg aggcggcggt   1740
agctccagtg cccactatgc agtcaacaac cagttcacca tgggtggccc tgccatctct   1800
atggcctcgc ccatgtccat cccgaccaac accatgcact atgggagtta ggtgcctcca   1860
gccgcgacag cactgcgcac tgacagcacc aggaaaccaa atcaagtcca ggcccggcac   1920
agccagtggc tgttccccct tgttctggag aagttgttga acacccggtc acagcctcct   1980
tgctatggga acttggacaa ttttgtacac gatgtcgccg ctgccctcaa gtacccccag   2040
cccaaccttt ggtcccgagc gcgtgttgct gccatacttt acatgagatc ctgttggggc   2100
agccctcatc ctgttctgta ctctccactc tgacctggct ttgacatctg ctggaagagg   2160
caagtcctcc cccaaccccc acagctgcac ctgaccaggc aggaggaggc cagcagctgc   2220
caccacagac ctggcagcac ccaccccaca acccgtcctt gcacctcccc tcacctgggg   2280
tggcagcaca gccagctgga cctctccttc aactaccagg ccacatggtc accatgggcg   2340
tgacatgctg ctttttttaa ttttattttt ttacgaaaag aaccagtgtc aacccacaga   2400
ccctctgaga aacccggctg gcgcgccaag ccagcagccc ctgttcctag gcccagaggt   2460
tctaggtgag ggtggccct gtcaagcctt cagagtgggc acagcccctc ccaccaaagg    2520
gttcacctca aacttgaatg tacaaaccac ccagctgtcc aaaggcctag tccctacttt   2580
ctgctactgt cctgtcctga gccctgaagg cccccctcca tcaaaagctt gaacaggcag   2640
cccagagtgt gtcaccctgg gctactgggg cagacaagaa acctcaaaga tctgtcacac   2700
acacacaagg aaggcgtcct ctcctgatag ctgacatagg cctgtgtgtt gcgttcacat   2760
tcatgttcta cttaatcctc tcaagacagc aaccctggga aggagcctcg cagggacctc   2820
cccagacaag aagaaaagca aacaaggaag ggtgattaat aagcacaggc agtttcccct   2880
attcccttac cctagagtcc ccacctgaat ggccacagcc tgccacagga accccttggc   2940
aaaggctgga gctgctctgt gccaccctcc tgacctgtca gggaatcaca gggccctcag   3000
gcagctggga accaggctct ctcctgtcca tcagtaatac tccttgctcg gatggccctc   3060
ccccaccttt atataaattc tctggatcac ctttgcatag aaaataaaag tgtttgcttt   3120
gtaa                                                                3124
```

<210> SEQ ID NO 2
<211> LENGTH: 2954
<212> TYPE: DNA
<213> ORGANISM: Homo sapiens

<400> SEQUENCE: 2

```
cggcggcggc ggcggcggcg gcggcggcgg cggcggcggc ggcggcggca gcggcggcgg      60

cctgggcccg ggcgcagcgg cggcggcggc ggggcctgga gccggatcta agatggcagc     120

ggcggcggcg gcggtggggc cgggcgcggg cggcgcgggg tcggcggtcc cgggcggcgc     180

ggggccctgc gctaccgtgt cggtgttccc cggcgcccgc ctcctcacca tcggcgacgc     240

gaacggcgag atccagcggc acgcggagca gcaggcgctg cgcctcgagg tgcgcgccgg     300

cccggactcg gcgggcatcg ccctctacag ccatgaagat gtgtgtgtct ttaagtgctc     360

agtgtcccga gagacagagt gcagccgtgt gggcaagcag tccttcatca tcaccctggg     420

ctgcaacagc gtcctcatcc agttcgccac acccaacgat ttctgttcct tctacaacat     480

cctgaaaacc tgccggggcc acaccctgga gcggtctgtg ttcagcgagc ggacggagga     540

gtcttctgcc gtgcagtact tccagtttta tggctacctg tcccagcagc agaacatgat     600

gcaggactac gtgcggacag gcacctacca gcgcgccatc ctgcaaaacc acaccgactt     660

caaggacaag atcgttcttg atgttggctg tggctctggg atcctgtcgt tttttgccgc     720

ccaagctgga gcacggaaaa tctacgcggt ggaggccagc accatggccc agcacgctga     780

ggtcttggtg aagagtaaca acctgacgga ccgcatcgtg gtcatcccgg gcaaggtgga     840

ggaggtgtca ctccccgagc aggtggacat catcatctcg gagcccatgg gctacatgct     900

cttcaacgag cgcatgctgg agagctacct ccacgccaag aagtacctga agcccagcgg     960

aaacatgttt cctaccattg gtgacgtcca ccttgcaccc ttcacggatg aacagctcta    1020

catggagcag ttcaccaagg ccaacttctg gtaccagcca tctttccatg gagtggacct    1080

gtcggccctc cgaggtgccg cggtggatga gtatttccgg cagcctgtgg tggacacatt    1140

tgacatccgg atcctgatgg ccaagtctgt caagtacacg gtgaacttct tagaagccaa    1200

agaaggagat ttgcacagga tagaaatccc attcaaattc cacatgctgc attcagggct    1260

ggtccacggc ctggctttct ggtttgacgt tgctttcatc ggctccataa tgaccgtgtg    1320

gctgtccaca gccccgacag agcccctgac ccactggtac caggtgcggt gcctgttcca    1380

gtcaccactg ttcgccaagg caggggacac gctctcaggg acatgtctgc ttattgccaa    1440

caaaagacag agctacgaca tcagtattgt ggcccaggtg gaccagaccg gctccaagtc    1500

cagtaacctc ctggatctga aaaacccctt ctttagatac acgggcacaa cgccctcacc    1560

cccacccggc tcccactaca catctccctc ggaaaacatg tggaacacgg gcagcaccta    1620

caacctcagc agcgggatgg ccgtggcagg gatgccgacc gcctatgact tgagcagtgt    1680

tattgccagt ggctccagcg tgggccacaa caacctgatt cctttagcca acacggggat    1740

tgtcaatcac acccactccc ggatgggctc cataatgagc acggggattg tccaagggtc    1800

ctccggcgcc cagggcagtg gtggtggcag cacgagtgcc cactatgcag tcaacagcca    1860

gttcaccatg ggcggccccg ccatctccat ggcgtcgccc atgtccatcc cgaccaacac    1920

catgcactac gggagctagg ggcccgcccc gcggactgac agcaccagga aaccaaatga    1980

tgtccctgcc cgccgccccc gccgggcggc tttcccccttt gtactggaga agctcgaaca    2040

cccggtcaca gctctctttg ctatgggaac tgggacactt ttttacacga tgttgccgcc    2100

gtccccaccc taacccccac ctcccggccc tgagcgtgtg tcgctgccat atttacaca     2160
```

-continued

```
aaatcatgtt gtgggagccc tcgtccccc tcctgcccgc tctaccctga cctgggcttg   2220

tcatctgctg gaacaggcgc catggggcct gccagccctg cctgccaggt cccttagcac   2280

ctgtccccct gcctgtctcc agtgggaagg tagcctggcc aggcggggcc tccccttcga   2340

cgaccaggcc tcggtcacaa cggacgtgac atgctgcttt ttttaatttt atttttttat   2400

gaaaagaacc agtgtcaatc cgcagaccct ctgtgaagcc aggccggccg ggccgagcca   2460

gcagcccctc tccctagact cagaggcgcc gcggggaggg gtggccccgc cgaggcttca   2520

ggggccccct ccccaccaaa gggttcacct cacacttgaa tgtacaaccc accccactgt   2580

cgggaaggcc tccgtcctcg gcccctgcct cttgctgctg tcctgtcccc gagcccctgc   2640

aggtccccc ccgcccccc actcaagagt tagagcaggt ggctgcaggc cttgggcccg   2700

gagggaaggc cactgccggc cacttggggc agacacagac acctcaagga tctgtcacgg   2760

aaggcgtcct ttttccttgt agctaacgtt aggcctgagt agctcccctc catccttgta   2820

gacgctccag tccctactac tgtgacggca tttccatccc tcccctgccc gggaagggac   2880

cttgcaggga cctctccctc caaaaaaaga aaaaaagaaa aagaaagaaa aaataaatga   2940

ggaaacgtgt tgca                                                    2954
```

<210> SEQ ID NO 3
<211> LENGTH: 2143
<212> TYPE: DNA
<213> ORGANISM: Homo sapiens

<400> SEQUENCE: 3

```
cgcatcgtgg tcatcccggg caaggtggag gaggtgtcac tccccgagca ggtggacatc     60

atcatctcgg agcccatggg ctacatgctc ttcaacgagc gcatgctgga gagctacctc    120

cacgccaaga agtacctgaa gcccagcgga aacatgtttc ctaccattgg tgacgtccac    180

cttgcaccct tcacggatga acagctctac atggagcagt tcaccaaggc caacttctgg    240

taccagccat ctttccatgg agtggacctg tcggccctcc gaggtgccgc ggtggatgag    300

tatttccggc agcctgtggt ggacacattt gacatccgga tcctgatggc caagtctgtc    360

aagtacacgg tgaacttctt agaagccaaa gaaggagatt tgcacaggat agaaatccca    420

ttcaaattcc acatgctgca ttcagggctg gtccacggcc tggctttctg gtttgacgtt    480

gctttcatcg gctccataat gaccgtgtgg ctgtccacag ccccgacaga gcccctgacc    540

cactggtacc aggtgcggtg cctgttccag tcaccactgt tcgccaaggc aggggacacg    600

ctctcaggga catgtctgct tattgccaac aaaagacaga gctacgacat cagtattgtg    660

gcccaggtgg accagaccgg ctccaagtcc agtaacctcc tggatctgaa aaaccccttc    720

tttagataca cgggcacaac gccctcaccc ccacccggct cccactacac atctccctcg    780

gaaaacatgt ggaacacggg cagcacctac aacctcagca gcgggatggc cgtggcaggg    840

atgccgaccg cctatgactt gagcagtgtt attgccagtg gctccagcgt gggccacaac    900

aacctgattc ctttagccaa cacggggatt gtcaatcaca cccactcccg gatgggctcc    960

ataatgagca cggggattgt ccaaggggtc ctccggcgcc cagggcagtg gtggtggcag   1020

cacgagtgcc cactatgcag tcaacagcca gttcaccatg ggcggccccg ccatctccat   1080

ggcgtcgccc atgtccatcc cgaccaacac catgcactac gggagctagg ggcccgcccc   1140

gcggactgac agcaccagga aaccaaatga tgtccctgcc cgccgccccc gccgggcggc   1200

tttccccctt gtactggaga agctcgaaca cccggtcaca gctctctttg ctatgggaac   1260

tgggacactt ttttacacga tgttgccgcc gtccccaccc taacccccac ctcccggccc   1320
```

```
tgagcgtgtg tcgctgccat attttacaca aaatcatgtt gtgggagccc tcgtcccccc   1380

tcctgcccgc tctaccctga cctgggcttg tcatctgctg gaacaggcgc catggggcct   1440

gccagccctg cctgccaggt cccttagcac ctgtccccct gcctgtctcc agtgggaagg   1500

tagcctggcc aggcggggcc tccccttcga cgaccaggcc tcggtcacaa cggacgtgac   1560

atgctgcttt ttttaatttt attttttat gaaaagaacc agtgtcaatc cgcagaccct   1620

ctgtgaagcc aggccggccg ggccgagcca gcagcccctc tccctagact cagaggcgcc   1680

gcggggaggg gtggccccgc cgaggcttca ggggccccct ccccaccaaa gggttcacct   1740

cacacttgaa tgtacaaccc accccactgt cgggaaggcc tccgtcctcg gcccctgcct   1800

cttgctgctg tcctgtcccc gagcccctgc aggtcccccc ccgccccccc actcaagagt   1860

tagagcaggt ggctgcaggc cttgggcccg gagggaaggc cactgccggc cacttggggc   1920

agacacagac acctcaagga tctgtcacgg aaggcgtcct tttccttgt agctaacgtt   1980

aggcctgagt agctcccctc catccttgta gacgctccag tccctactac tgtgacggca   2040

tttccatccc tcccctgccc gggaagggac cttgcaggga cctctccctc caaaaaaaga   2100

aaaaaagaaa aagaaagaaa aaataaatga ggaaacgtgt tgc                      2143
```

<210> SEQ ID NO 4
<211> LENGTH: 2506
<212> TYPE: DNA
<213> ORGANISM: Homo sapiens

<400> SEQUENCE: 4

```
agatggcgcg gagcgggagg cggccctgga gcgaccccgg aggactaagc gggaacggga     60

ccagctgtac tacgagtgct actcggacgt ttcggtccac gaggagatga tcgcggaccg    120

cgtccgcacc gatgcctacc gcctgggtat ccttcggaac tgggcagcac tgcgaggcaa    180

gacggtactg gacgtgggcg cgggcaccgg cattctgagc atcttctgtg cccaggccgg    240

ggcccggcgc gtgtacgcgg tagaggccag cgccatctgg caacaggccc gggaggtggt    300

gcggttcaac gggctggagg accgggtgca cgtcctgccg ggaccagtgg agactgtaga    360

gttgccggaa caggtggatg ccatcgtgag cgagtggatg ggctacggac tcctgcacga    420

gtccatgctg agctccgtcc tccacgcgcg aaccaagtgg ctgaaggagg gcggtcttct    480

cctgccggcc tccgccgagc tcttcatagc cccccatcagc gaccagatgc tggaatggcg    540

cctgggcttc tggagccagg tgaagcagca ctatggtgtg gacatgagct gcctggaggg    600

cttcgccacg cgctgtctca tgggccactc ggagatcgtt gtgcagggat tgtccggcga    660

ggacgtgctg gcccggccgc agcgctttgc tcagctagag ctctcccgcg ccggcttgga    720

gcaggagctg gaggccggag tgggcgggcg cttccgctgc agctgctatg gctcggcgcc    780

catgcatggc tttgccatct ggttccaggt gaccttccct ggaggggagt cggagaaacc    840

cctggtgctg tccacctcgc cttttcaccc ggccactcac tggaaacagg cgctcctcta    900

cctgaacgag ccggtgcaag tggagcaaga cacggacgtt tcaggagaga tcacgctgct    960

gccctcccgg gacaaccccc gtcgcctgcg cgtgctgctg cgctacaaag tgggagacca   1020

ggaggagaag accaaagact ttgccatgga ggactgagcg ttgccttttc tcccagctac   1080

ctcccaaagc agcctgacct gcgtgggaga ggcgtagcga ggtcggaggg gaaagggaga   1140

tcccacgtgc aagtaggggg aatatctccc ccttttccct catagcctct agggagggag   1200

agtgacttca ttctccattt gaagagattc ttctggtgat gtttacttaa aaagtgatcc   1260
```

-continued

```
ccctcaacaa cggatacagc gtgcttatta ttgggcattt agcctcaaaa gcatgtagta   1320
ccaagcactt gtatttccgt atattttgtt tcgcggggga gtgaggggga agaacacgga   1380
tgaaaatgtc agtttttgaa gggtccatgc acatccctga cacctcacac cttatctaag   1440
tctgaagctg ggagaaaggg ggttcattta gacttcatac atttccagta cgactttagt   1500
atctctccag agccatattt tctcagtccg aattaattcc ccctccctag gtgcctgtag   1560
gctatggtac ttcttcctca ttgttttcta ggtaaacttc actactggta attaagggga   1620
aggatatgag gaagcagttt aaatagccct gttctcatta ctctgaccac atacatcata   1680
gggtgctaaa gttgatgaac acattaatcc gttaagtaaa atggactttg taattgtaca   1740
gcatacctaa gaaactcaga aggtgcattt aagagagaga cctgaaagaa atagtatgga   1800
tttttaaaaa ttcttgtctc tactattata accaaaaaat atttcttgta tgtcccataa   1860
aaatatttgt gtaattctta tgaaacaggc tggtagagga ggtttctgag cctagcccaa   1920
gggcttattc atcaccatgg gtaaattatt taaactcact taattaagga aaatattttc   1980
ccagctagaa aagtatactc attctcattt aaactctctc atttggaggg atcatgtgag   2040
ttggcctact tacaagtagt gaaagttccc ttttcagttt tgttttgttt tgttttgttt   2100
ttctctttca ctcagccaaa tgtgaaagtt gtgaatttag gaaaatcact tgtaatgaag   2160
tgtgaatctt gttatcaaat ttatttctct gatgtttcct tccttatcct tgtagccaat   2220
aaaacattga cattctcacg ttttatagat gaggtaaaaa gtcttgtgtg ctgtgagtta   2280
taatgctttt gcctttttaa tattattagt tcttaagtgt tacagcccct tcagaatata   2340
acttcaggac aattcaaact atgcttaatg tatgattttc gagcttctgt atgctaagaa   2400
aataggtgtg aaaaactggt gttctgaaat agcctaacat ttattgtaat tctgaatttt   2460
ctgccctttt attcattgca tattaaagta ttagagtata aaaact                  2506
```

<210> SEQ ID NO 5
<211> LENGTH: 2506
<212> TYPE: DNA
<213> ORGANISM: Homo sapiens

<400> SEQUENCE: 5

```
agatggcgcg gagcgggagg cggccctgga gcgaccccgg aggactaagc gggaacggga     60
ccagctgtac tacgagtgct actcggacgt ttcggtccac gaggagatga tcgcggaccg    120
cgtccgcacc gatgcctacc gcctgggtat ccttcggaac tgggcagcac tgcgaggcaa    180
gacggtactg gacgtgggcg cgggcaccgg cattctgagc atcttctgtg cccaggccgg    240
ggcccggcgc gtgtacgcgg tagaggccag cgccatctgg caacaggccc gggaggtggt    300
gcggttcaac gggctggagg accgggtgca cgtcctgccg ggaccagtgg agactgtaga    360
gttgccggaa caggtggatg ccatcgtgag cgagtggatg ggctacggac tcctgcacga    420
gtccatgctg agctccgtcc tccacgcgcg aaccaagtgg ctgaaggagg gcggtcttct    480
cctgccggcc tccgccgagc tcttcatagc ccccatcagc gaccagatgc tggaatggcg    540
cctgggcttc tggagccagg tgaagcagca ctatggtgtg gacatgagct gcctggaggg    600
cttcgccacg cgctgtctca tgggccactc ggagatcgtt gtgcagggat tgtccggcga    660
ggacgtgctg gcccggccgc agcgctttgc tcagctagag ctctcccgcg ccggcttgga    720
gcaggagctg gaggccggag tgggcgggcg cttccgctgc agctgctatg gctcggcgcc    780
catgcatggc tttgccatct ggttccaggt gaccttccct ggaggggagt cggagaaacc    840
cctggtgctg tccacctcgc cttttcaccc ggccactcac tggaaacagg cgctcctcta    900
```

```
cctgaacgag ccggtgcaag tggagcaaga cacggacgtt tcaggagaga tcacgctgct    960

gccctcccgg gacaaccccc gtcgcctgcg cgtgctgctg cgctacaaag tgggagacca   1020

ggaggagaag accaaagact ttgccatgga ggactgagcg ttgccttttc tcccagctac   1080

ctcccaaagc agcctgacct gcgtgggaga ggcgtagcga ggtcggaggg gaaagggaga   1140

tcccacgtgc aagtaggggg aatatctccc ccttttccct catagcctct agggagggag   1200

agtgacttca ttctccattt gaagagattc ttctggtgat gtttacttaa aaagtgatcc   1260

ccctcaacaa cggatacagc gtgcttatta ttgggcattt agcctcaaaa gcatgtagta   1320

ccaagcactt gtatttccgt atattttgtt tcgcggggga gtgagggggga agaacacgga  1380

tgaaaatgtc agtttttgaa gggtccatgc acatccctga cacctcacac cttatctaag   1440

tctgaagctg gggagaaagg ggttcattta gacttcatac atttccagta cgactttagt   1500

atctctccag agccatattt tctcagtccg aattaattcc ccctccctag gtgcctgtag   1560

gctatggtac ttcttcctca ttgttttcta ggtaaacttc actactggta attaagggga   1620

aggatatgag gaagcagttt aaatagccct gttctcatta ctctgaccac atacatcata   1680

gggtgctaaa gttgatgaac acattaatcc gttaagtaaa atggactttg taattgtaca   1740

gcatacctaa gaaactcaga aggtgcattt aagagagaga cctgaaagaa atagtatgga   1800

tttttaaaaa ttcttgtctc tactattata accaaaaaat atttcttgta tgtcccataa   1860

aaatatttgt gtaattctta tgaaacaggc tggtagagga ggtttctgag cctagcccaa   1920

gggcttattc atcaccatgg gtaaattatt taaactcact taattaagga aaatattttc   1980

ccagctagaa aagtatactc attctcattt aaactctctc atttggaggg atcatgtgag   2040

ttggcctact tacaagtagt gaaagttccc ttttcagttt tgttttgttt tgttttgttt   2100

ttctctttca ctcagccaaa tgtgaaagtt gtgaatttag gaaaatcact tgtaatgaag   2160

tgtgaatctt gttatcaaat ttatttctct gatgtttcct tccttatcct tgtagccaat   2220

aaaacattga cattctcacg ttttatagat gaggtaaaaa gtcttgtgtg ctgtgagtta   2280

taatgctttt gcctttttaa tattattagt tcttaagtgt tacagcccct tcagaatata   2340

acttcaggac aattcaaact atgcttaatg tatgattttc gagcttctgt atgctaagaa   2400

aataggtgtg aaaaactggt gttctgaaat agcctaacat ttattgtaat tctgaatttt   2460

ctgccctttt attcattgca tattaaagta ttagagtata aaaact                  2506
```

<210> SEQ ID NO 6
<211> LENGTH: 2577
<212> TYPE: DNA
<213> ORGANISM: Homo sapiens

<400> SEQUENCE: 6

```
atgtcgcagc ccaagaaaag aaagcttgag tcgggggcg gcggcgaagg aggggaggga      60

actgaagagg aagatggcgc ggagcgggag gcggccctgg agcgaccccg gaggactaag    120

cgggaacggg accagctgta ctacgagtgc tactcggacg tttcggtcca cgaggagatg    180

atcgcggacc gcgtccgcac cgatgcctac cgcctgggta tccttcggaa ctgggcagca    240

ctgcgaggca agacggtact ggacgtgggc gcgggcaccg gcattctgag catcttctgt    300

gcccaggccg ggcccggcg cgtgtacgcg gtagaggcca gcgccatctg gcaacaggcc    360

cgggaggtgg tgcggttcaa cgggctggag gaccgggtgc acgtcctgcc gggaccagtg    420

gagactgtag agttgccgga acaggtggat gccatcgtga gcgagtggat gggctacgga    480
```

-continued

```
ctcctgcacg agtccatgct gagctccgtc ctccacgcgc gaaccaagtg gctgaaggag    540

ggcggtcttc tcctgccggc ctccgccgag ctcttcatag cccccatcag cgaccagatg    600

ctggaatggc gcctgggctt ctggagccag gtgaagcagc actatggtgt ggacatgagc    660

tgcctggagg gcttcgccac gcgctgtctc atgggccact cggagatcgt tgtgcaggga    720

ttgtccggcg aggacgtgct ggcccggccg cagcgctttg ctcagctaga gctctcccgc    780

gccggcttgg agcaggagct ggaggccgga gtgggcgggc gcttccgctg cagctgctat    840

ggctcggcgc ccatgcatgg ctttgccatc tggttccagg tgaccttccc tggaggggag    900

tcggagaaac ccctggtgct gtccacctcg ccttttcacc cggccactca ctggaaacag    960

gcgctcctct acctgaacga gccggtgcaa gtggagcaag acacggacgt ttcaggagag   1020

atcacgctgc tgccctcccg ggacaacccc cgtcgcctgc gcgtgctgct gcgctacaaa   1080

gtgggagacc aggaggagaa gaccaaagac tttgccatgg aggactgagc gttgcctttt   1140

ctcccagcta cctcccaaag cagcctgacc tgcgtgggag aggcgtagcg aggtcggagg   1200

ggaaagggag atcccacgtg caagtagggg gaatatctcc cccttttccc tcatagcctc   1260

tagggaggga gagtgacttc attctccatt tgaagagatt cttctggtga tgtttactta   1320

aaaagtgatc cccctcaaca acggatacag cgtgcttatt attgggcatt tagcctcaaa   1380

agcatgtagt accaagcact tgtatttccg tatattttgt ttcgcggggg agtgaggggg   1440

aagaacacgg atgaaaatgt cagtttttga agggtccatg cacatccctg acacctcaca   1500

ccttatctaa gtctgaagct ggggagaaag ggttcattt agacttcata catttccagt    1560

acgactttag tatctctcca gagccatatt ttctcagtcc gaattaattc cccctcccta   1620

ggtgcctgta ggctatggta cttcttcctc attgttttct aggtaaactt cactactggt   1680

aattaagggg aaggatatga ggaagcagtt taaatagccc tgttctcatt actctgacca   1740

catacatcat agggtgctaa agttgatgaa cacattaatc cgttaagtaa aatggacttt   1800

gtaattgtac agcataccta agaaactcag aaggtgcatt taagagagag acctgaaaga   1860

aatagtatgg atttttaaaa attcttgtct ctactattat aaccaaaaaa tatttcttgt   1920

atgtcccata aaaatatttg tgtaattctt atgaaacagg ctggtagagg aggtttctga   1980

gcctagccca agggcttatt catcaccatg ggtaaattat ttaaactcac ttaattaagg   2040

aaaatatttt cccagctaga aaagtatact cattctcatt taaactctct catttggagg   2100

gatcatgtga gttggcctac ttacaagtag tgaaagttcc cttttcagtt ttgttttgtt   2160

ttgttttgtt tttctctttc actcagccaa atgtgaaagt tgtgaattta ggaaaatcac   2220

ttgtaatgaa gtgtgaatct tgttatcaaa tttatttctc tgatgtttcc ttccttatcc   2280

ttgtagccaa taaaacattg acattctcac gttttataga tgaggtaaaa agtcttgtgt   2340

gctgtgagtt ataatgcttt tgccttttta atattattag ttcttaagtg ttacagcccc   2400

ttcagaatat aacttcagga caattcaaac tatgcttaat gtatgatttt cgagcttctg   2460

tatgctaaga aaataggtgt gaaaaactgg tgttctgaaa tagcctaaca tttattgtaa   2520

ttctgaattt tctgcccttt tattcattgc atattaaagt attagagtat aaaaact      2577
```

```
<210> SEQ ID NO 7
<211> LENGTH: 2234
<212> TYPE: DNA
<213> ORGANISM: Homo sapiens

<400> SEQUENCE: 7

ggcacgaggc ggaggactaa gcgggaacgg gaccagctgt actacgagtg ctactcggac     60
```

-continued

```
gtttcggtcc acgaggagat gatcgcggac cgcgtccgca ccgatgccta ccgcctgggt    120
atccttcgga actgggcagc actgcgaggc aagacggtac tggacgtggg cgcgggcacc    180
ggcattctga gcatcttctg tgcccaggcc ggggcccggc gcgtgtacgc ggtagaggcc    240
agcgccatct ggcaacaggc ccgggaggtg gtgcggttca acgggctgga ggaccgggtg    300
cacgtcctgc cgggaccagt ggagactgta gagttgccgg aacaggtgga tgccatcgtg    360
agcgagtgga tgggctacgg actcctgcac gagtccatgc tgagctccgt cctccacgcg    420
cgaaccaagt ggctgaagga gggcggtctt ctcctgccgg cctccgccga gctcttcata    480
gcccccatca gcgaccagat gctggaatgg cgcctgggct tctggagcca ggtgaagcag    540
cactatggtg tggacatgag ctgcctggag ggcttcgcca cgcgctgtct catgggccac    600
tcggagatcg ttgtgcaggg attgtccggc gaggacgtgc tggcccggcc gcagcgcttt    660
gctcagctag agctctcccg cgccggcttg gagcaggagc tggaggccgg agtgggcggg    720
cgcttccgct gcagctgcta tggctcggcg cccatgcatg gctttgccat ctggttccag    780
gtgaccttcc ctggaggga gtcggagaaa cccctggtgc tgtccacctc gccttttcac    840
ccggccactc actggaaaca ggcgctcctc tacctgaacg agccggtgca agtggagcaa    900
gacacggacg tttcaggaga gatcacgctg ctgccctccc gggacaaccc ccgtcgcctg    960
cgcgtgctgc tgcgctacaa agtgggagac caggaggaga agaccaaaga ctttgccatg   1020
gaggactgag cgttgccttt tctcccagct acctcccaaa gcagcctgac ctgcgtggga   1080
gaggcgtagc gaggtcggag gggaaaggga gatcccacgt gcaagtaggg ggaatatctc   1140
cctcttttcc ctcatagcct ctagggaggg agagtgactt cattctccat ttgaagagat   1200
tcttctggtg atgtttactt aaaaagtgat ccccctcaac aacggataca gcgtgcttat   1260
tattgggcat ttagcctcaa aagcatgtag taccaagcac ttgtatttcc gtatattttg   1320
tttcgcgggg gagtgagggg gaagaacacg gatgaaaatg tcagtttttg aagggtccat   1380
gcacatccct gacacctcac accttatcta agtctgaagc tggggagaaa ggggttcatt   1440
tagacttcat acatttccag tacgacttta gtatctctcc agagccatat tttctcagtc   1500
cgaattaatt ccccctccct aggtgcctgt aggctatggt acttcttcct cattgttttc   1560
taggtaaact tcactactgg taattaaggg gaaggatatg aggaagcagt ttaaatagcc   1620
ctgttctcat tactctgacc acatacatca tagggtgcta aagttgatga acacattaat   1680
ccgttaagta aaatggactt tgtaattgta cagcatacct aagaaactca gaaggtgcat   1740
ttaagagaga gacctgaaag aaatagtatg gatttttaaa aattcttgtc tctactatta   1800
taaccaaaaa atatttcttg tatgtcccat aaaaatattt gtgtaattct tatgaaacag   1860
gctggtagag gaggtttctg agcctagccc aagggcttat tcatcaccat gggtaaatta   1920
tttaaactca cttaattaag gaaaatattt tcccagctag aaaagtatac tcattctcat   1980
ttaaactctc tcatttggag ggatcatgtg agttggccta cttacaagta gtgaaagttc   2040
ccttttcagt tttgttttgt tttgttttgt ttttctcttt cactcagcca aatgtgaaag   2100
ttgtgaattt aggaaaatca cttgtaatga agtgtgaatc ttgttatcaa atttatttct   2160
ctgatgtttc cttccttatc cttgtagcca ataaaacatt gacattctca cgttttaaaa   2220
aaaaaaaaaa aaaa                                                     2234
```

<210> SEQ ID NO 8
<211> LENGTH: 608
<212> TYPE: PRT

<213> ORGANISM: Mus musculus

<400> SEQUENCE: 8

```
Met Ala Ala Ala Ala Ala Thr Ala Val Gly Pro Gly Ala Gly Ser Ala
1               5                   10                  15

Gly Val Ala Gly Pro Gly Gly Ala Gly Pro Cys Ala Thr Val Ser Val
            20                  25                  30

Phe Pro Gly Ala Arg Leu Leu Thr Ile Gly Asp Ala Asn Gly Glu Ile
        35                  40                  45

Gln Arg His Ala Glu Gln Gln Ala Leu Arg Leu Glu Val Arg Ala Gly
    50                  55                  60

Pro Asp Ala Ala Gly Ile Ala Leu Tyr Ser His Glu Asp Val Cys Val
65                  70                  75                  80

Phe Lys Cys Ser Val Ser Arg Glu Thr Glu Cys Ser Arg Val Gly Arg
                85                  90                  95

Gln Ser Phe Ile Ile Thr Leu Gly Cys Asn Ser Val Leu Ile Gln Phe
            100                 105                 110

Ala Thr Pro His Asp Phe Cys Ser Phe Tyr Asn Ile Leu Lys Thr Cys
        115                 120                 125

Arg Gly His Thr Leu Glu Arg Ser Val Phe Ser Glu Arg Thr Glu Glu
    130                 135                 140

Ser Ser Ala Val Gln Tyr Phe Gln Phe Tyr Gly Tyr Leu Ser Gln Gln
145                 150                 155                 160

Gln Asn Met Met Gln Asp Tyr Val Arg Thr Gly Thr Tyr Gln Arg Ala
                165                 170                 175

Ile Leu Gln Asn His Thr Asp Phe Lys Asp Lys Ile Val Leu Asp Val
            180                 185                 190

Gly Cys Gly Ser Gly Ile Leu Ser Phe Phe Ala Ala Gln Ala Gly Ala
        195                 200                 205

Arg Lys Ile Tyr Ala Val Glu Ala Ser Thr Met Ala Gln His Ala Glu
    210                 215                 220

Val Leu Val Lys Ser Asn Asn Leu Thr Asp Arg Ile Val Val Ile Pro
225                 230                 235                 240

Gly Lys Val Glu Glu Val Ser Leu Pro Glu Gln Val Asp Ile Ile Ile
                245                 250                 255

Ser Glu Pro Met Gly Tyr Met Leu Phe Asn Glu Arg Met Leu Glu Ser
            260                 265                 270

Tyr Leu His Ala Lys Lys Tyr Leu Lys Pro Ser Gly Asn Met Phe Pro
        275                 280                 285

Thr Ile Gly Asp Val His Leu Ala Pro Phe Thr Asp Glu Gln Leu Tyr
    290                 295                 300

Met Glu Gln Phe Thr Lys Ala Asn Phe Arg Tyr Gln Pro Ser Phe His
305                 310                 315                 320

Gly Val Asp Leu Ser Ala Leu Arg Gly Ala Ala Val Asp Glu Tyr Phe
                325                 330                 335

Arg Gln Pro Val Val Asp Thr Phe Asp Ile Arg Ile Leu Met Ala Lys
            340                 345                 350

Ser Val Lys Tyr Thr Val Asn Phe Leu Glu Ala Lys Glu Gly Asp Leu
        355                 360                 365

His Arg Ile Glu Ile Pro Phe Lys Phe His Met Leu His Ser Gly Leu
    370                 375                 380

Val His Gly Leu Ala Phe Trp Phe Asp Val Ala Phe Ile Gly Ser Ile
385                 390                 395                 400
```

-continued

```
Met Thr Val Trp Leu Ser Thr Ala Pro Thr Glu Pro Leu Thr His Trp
                405                 410                 415

Tyr Gln Val Arg Cys Leu Phe Gln Ser Pro Leu Phe Ala Lys Ala Gly
            420                 425                 430

Asp Thr Leu Ser Gly Thr Cys Leu Leu Ile Ala Asn Lys Arg Gln Ser
        435                 440                 445

Tyr Asp Ile Ser Ile Val Ala Gln Val Asp Gln Thr Gly Ser Lys Ser
    450                 455                 460

Ser Asn Leu Leu Asp Leu Lys Asn Pro Phe Phe Arg Tyr Thr Gly Thr
465                 470                 475                 480

Thr Pro Ser Pro Pro Pro Gly Ser His Tyr Thr Ser Pro Ser Glu Asn
                485                 490                 495

Met Trp Asn Thr Gly Ser Thr Tyr Asn Leu Ser Ser Gly Val Ala Val
            500                 505                 510

Ala Gly Met Pro Thr Ala Tyr Asp Leu Ser Ser Val Ile Ala Gly Gly
        515                 520                 525

Ser Ser Val Gly His Asn Asn Leu Ile Pro Leu Ala Asn Thr Gly Ile
    530                 535                 540

Val Asn His Thr His Ser Arg Met Gly Ser Ile Met Ser Thr Gly Ile
545                 550                 555                 560

Val Gln Gly Ser Ser Gly Ala Gln Gly Gly Gly Gly Ser Ser Ser Ala
                565                 570                 575

His Tyr Ala Val Asn Asn Gln Phe Thr Met Gly Gly Pro Ala Ile Ser
            580                 585                 590

Met Ala Ser Pro Met Ser Ile Pro Thr Asn Thr Met His Tyr Gly Ser
        595                 600                 605
```

<210> SEQ ID NO 9
<211> LENGTH: 608
<212> TYPE: PRT
<213> ORGANISM: Homo sapiens

<400> SEQUENCE: 9

```
Met Ala Ala Ala Ala Ala Ala Val Gly Pro Gly Ala Gly Gly Ala Gly
1               5                   10                  15

Ser Ala Val Pro Gly Gly Ala Gly Pro Cys Ala Thr Val Ser Val Phe
            20                  25                  30

Pro Gly Ala Arg Leu Leu Thr Ile Gly Asp Ala Asn Gly Glu Ile Gln
        35                  40                  45

Arg His Ala Glu Gln Gln Ala Leu Arg Leu Glu Val Arg Ala Gly Pro
    50                  55                  60

Asp Ser Ala Gly Ile Ala Leu Tyr Ser His Glu Asp Val Cys Val Phe
65                  70                  75                  80

Lys Cys Ser Val Ser Arg Glu Thr Glu Cys Ser Arg Val Gly Lys Gln
                85                  90                  95

Ser Phe Ile Ile Thr Leu Gly Cys Asn Ser Val Leu Ile Gln Phe Ala
            100                 105                 110

Thr Pro Asn Asp Phe Cys Ser Phe Tyr Asn Ile Leu Lys Thr Cys Arg
        115                 120                 125

Gly His Thr Leu Glu Arg Ser Val Phe Ser Glu Arg Thr Glu Glu Ser
    130                 135                 140

Ser Ala Val Gln Tyr Phe Gln Phe Tyr Gly Tyr Leu Ser Gln Gln Gln
145                 150                 155                 160

Asn Met Met Gln Asp Tyr Val Arg Thr Gly Thr Tyr Gln Arg Ala Ile
                165                 170                 175
```

-continued

```
Leu Gln Asn His Thr Asp Phe Lys Asp Lys Ile Val Leu Asp Val Gly
            180                 185                 190

Cys Gly Ser Gly Ile Leu Ser Phe Phe Ala Ala Gln Ala Gly Ala Arg
        195                 200                 205

Lys Ile Tyr Ala Val Glu Ala Ser Thr Met Ala Gln His Ala Glu Val
    210                 215                 220

Leu Val Lys Ser Asn Asn Leu Thr Asp Arg Ile Val Val Ile Pro Gly
225                 230                 235                 240

Lys Val Glu Glu Val Ser Leu Pro Glu Gln Val Asp Ile Ile Ile Ser
                245                 250                 255

Glu Pro Met Gly Tyr Met Leu Phe Asn Glu Arg Met Leu Glu Ser Tyr
            260                 265                 270

Leu His Ala Lys Lys Tyr Leu Lys Pro Ser Gly Asn Met Phe Pro Thr
        275                 280                 285

Ile Gly Asp Val His Leu Ala Pro Phe Thr Asp Glu Gln Leu Tyr Met
    290                 295                 300

Glu Gln Phe Thr Lys Ala Asn Phe Trp Tyr Gln Pro Ser Phe His Gly
305                 310                 315                 320

Val Asp Leu Ser Ala Leu Arg Gly Ala Ala Val Asp Glu Tyr Phe Arg
                325                 330                 335

Gln Pro Val Val Asp Thr Phe Asp Ile Arg Ile Leu Met Ala Lys Ser
            340                 345                 350

Val Lys Tyr Thr Val Asn Phe Leu Glu Ala Lys Glu Gly Asp Leu His
        355                 360                 365

Arg Ile Glu Ile Pro Phe Lys Phe His Met Leu His Ser Gly Leu Val
    370                 375                 380

His Gly Leu Ala Phe Trp Phe Asp Val Ala Phe Ile Gly Ser Ile Met
385                 390                 395                 400

Thr Val Trp Leu Ser Thr Ala Pro Thr Glu Pro Leu Thr His Trp Tyr
                405                 410                 415

Gln Val Arg Cys Leu Phe Gln Ser Pro Leu Phe Ala Lys Ala Gly Asp
            420                 425                 430

Thr Leu Ser Gly Thr Cys Leu Leu Ile Ala Asn Lys Arg Gln Ser Tyr
        435                 440                 445

Asp Ile Ser Ile Val Ala Gln Val Asp Gln Thr Gly Ser Lys Ser Ser
    450                 455                 460

Asn Leu Leu Asp Leu Lys Asn Pro Phe Phe Arg Tyr Thr Gly Thr Thr
465                 470                 475                 480

Pro Ser Pro Pro Pro Gly Ser His Tyr Thr Ser Pro Ser Glu Asn Met
                485                 490                 495

Trp Asn Thr Gly Ser Thr Tyr Asn Leu Ser Ser Gly Met Ala Val Ala
            500                 505                 510

Gly Met Pro Thr Ala Tyr Asp Leu Ser Ser Val Ile Ala Ser Gly Ser
        515                 520                 525

Ser Val Gly His Asn Asn Leu Ile Pro Leu Ala Asn Thr Gly Ile Val
    530                 535                 540

Asn His Thr His Ser Arg Met Gly Ser Ile Met Ser Thr Gly Ile Val
545                 550                 555                 560

Gln Gly Ser Ser Gly Ala Gln Gly Ser Gly Gly Gly Ser Thr Ser Ala
                565                 570                 575

His Tyr Ala Val Asn Ser Gln Phe Thr Met Gly Gly Pro Ala Ile Ser
            580                 585                 590
```

```
Met Ala Ser Pro Met Ser Ile Pro Thr Asn Thr Met His Tyr Gly Ser
        595                 600                 605


<210> SEQ ID NO 10
<211> LENGTH: 357
<212> TYPE: PRT
<213> ORGANISM: Homo sapiens

<400> SEQUENCE: 10

Met Gly Tyr Met Leu Phe Asn Glu Arg Met Leu Glu Ser Tyr Leu His
1               5                   10                  15

Ala Lys Lys Tyr Leu Lys Pro Ser Gly Asn Met Phe Pro Thr Ile Gly
            20                  25                  30

Asp Val His Leu Ala Pro Phe Thr Asp Glu Gln Leu Tyr Met Glu Gln
        35                  40                  45

Phe Thr Lys Ala Asn Phe Trp Tyr Gln Pro Ser Phe His Gly Val Asp
    50                  55                  60

Leu Ser Ala Leu Arg Gly Ala Ala Val Asp Glu Tyr Phe Arg Gln Pro
65                  70                  75                  80

Val Val Asp Thr Phe Asp Ile Arg Ile Leu Met Ala Lys Ser Val Lys
                85                  90                  95

Tyr Thr Val Asn Phe Leu Glu Ala Lys Glu Gly Asp Leu His Arg Ile
            100                 105                 110

Glu Ile Pro Phe Lys Phe His Met Leu His Ser Gly Leu Val His Gly
        115                 120                 125

Leu Ala Phe Trp Phe Asp Val Ala Phe Ile Gly Ser Ile Met Thr Val
    130                 135                 140

Trp Leu Ser Thr Ala Pro Thr Glu Pro Leu Thr His Trp Tyr Gln Val
145                 150                 155                 160

Arg Cys Leu Phe Gln Ser Pro Leu Phe Ala Lys Ala Gly Asp Thr Leu
                165                 170                 175

Ser Gly Thr Cys Leu Leu Ile Ala Asn Lys Arg Gln Ser Tyr Asp Ile
            180                 185                 190

Ser Ile Val Ala Gln Val Asp Gln Thr Gly Ser Lys Ser Ser Asn Leu
        195                 200                 205

Leu Asp Leu Lys Asn Pro Phe Phe Arg Tyr Thr Gly Thr Thr Pro Ser
    210                 215                 220

Pro Pro Pro Gly Ser His Tyr Thr Ser Pro Ser Glu Asn Met Trp Asn
225                 230                 235                 240

Thr Gly Ser Thr Tyr Asn Leu Ser Ser Gly Met Ala Val Ala Gly Met
                245                 250                 255

Pro Thr Ala Tyr Asp Leu Ser Ser Val Ile Ala Ser Gly Ser Ser Val
            260                 265                 270

Gly His Asn Asn Leu Ile Pro Leu Ala Asn Thr Gly Ile Val Asn His
        275                 280                 285

Thr His Ser Arg Met Gly Ser Ile Met Ser Thr Gly Ile Val Gln Gly
    290                 295                 300

Val Leu Arg Arg Pro Gly Gln Trp Trp Trp Gln His Glu Cys Pro Leu
305                 310                 315                 320

Cys Ser Gln Gln Pro Val His His Gly Arg Pro Arg His Leu His Gly
                325                 330                 335

Val Ala His Val His Pro Asp Gln His His Ala Leu Arg Glu Leu Gly
            340                 345                 350

Ala Arg Pro Ala Asp
        355
```

<210> SEQ ID NO 11
<211> LENGTH: 351
<212> TYPE: PRT
<213> ORGANISM: Homo sapiens

<400> SEQUENCE: 11

```
Asp Gly Ala Glu Arg Glu Ala Ala Leu Glu Arg Pro Arg Arg Thr Lys
1               5                   10                  15

Arg Glu Arg Asp Gln Leu Tyr Tyr Glu Cys Tyr Ser Asp Val Ser Val
            20                  25                  30

His Glu Glu Met Ile Ala Asp Arg Val Arg Thr Asp Ala Tyr Arg Leu
        35                  40                  45

Gly Ile Leu Arg Asn Trp Ala Ala Leu Arg Gly Lys Thr Val Leu Asp
    50                  55                  60

Val Gly Ala Gly Thr Gly Ile Leu Ser Ile Phe Cys Ala Gln Ala Gly
65                  70                  75                  80

Ala Arg Arg Val Tyr Ala Val Glu Ala Ser Ala Ile Trp Gln Gln Ala
                85                  90                  95

Arg Glu Val Val Arg Phe Asn Gly Leu Glu Asp Arg Val His Val Leu
            100                 105                 110

Pro Gly Pro Val Glu Thr Val Glu Leu Pro Glu Gln Val Asp Ala Ile
        115                 120                 125

Val Ser Glu Trp Met Gly Tyr Gly Leu Leu His Glu Ser Met Leu Ser
    130                 135                 140

Ser Val Leu His Ala Arg Thr Lys Trp Leu Lys Glu Gly Gly Leu Leu
145                 150                 155                 160

Leu Pro Ala Ser Ala Glu Leu Phe Ile Ala Pro Ile Ser Asp Gln Met
                165                 170                 175

Leu Glu Trp Arg Leu Gly Phe Trp Ser Gln Val Lys Gln His Tyr Gly
            180                 185                 190

Val Asp Met Ser Cys Leu Glu Gly Phe Ala Thr Arg Cys Leu Met Gly
        195                 200                 205

His Ser Glu Ile Val Val Gln Gly Leu Ser Gly Glu Asp Val Leu Ala
    210                 215                 220

Arg Pro Gln Arg Phe Ala Gln Leu Glu Leu Ser Arg Ala Gly Leu Glu
225                 230                 235                 240

Gln Glu Leu Glu Ala Gly Val Gly Gly Arg Phe Arg Cys Ser Cys Tyr
                245                 250                 255

Gly Ser Ala Pro Met His Gly Phe Ala Ile Trp Phe Gln Val Thr Phe
            260                 265                 270

Pro Gly Gly Glu Ser Glu Lys Pro Leu Val Leu Ser Thr Ser Pro Phe
        275                 280                 285

His Pro Ala Thr His Trp Lys Gln Ala Leu Leu Tyr Leu Asn Glu Pro
    290                 295                 300

Val Gln Val Glu Gln Asp Thr Asp Val Ser Gly Glu Ile Thr Leu Leu
305                 310                 315                 320

Pro Ser Arg Asp Asn Pro Arg Arg Leu Arg Val Leu Leu Arg Tyr Lys
                325                 330                 335

Val Gly Asp Gln Glu Glu Lys Thr Lys Asp Phe Ala Met Glu Asp
            340                 345                 350
```

<210> SEQ ID NO 12
<211> LENGTH: 316
<212> TYPE: PRT

<213> ORGANISM: Homo sapiens

<400> SEQUENCE: 12

```
Met Ile Ala Asp Arg Val Arg Thr Asp Ala Tyr Arg Leu Gly Ile Leu
1               5                   10                  15

Arg Asn Trp Ala Ala Leu Arg Gly Lys Thr Val Leu Asp Val Gly Ala
            20                  25                  30

Gly Thr Gly Ile Leu Ser Ile Phe Cys Ala Gln Ala Gly Ala Arg Arg
        35                  40                  45

Val Tyr Ala Val Glu Ala Ser Ala Ile Trp Gln Gln Ala Arg Glu Val
    50                  55                  60

Val Arg Phe Asn Gly Leu Glu Asp Arg Val His Val Leu Pro Gly Pro
65                  70                  75                  80

Val Glu Thr Val Glu Leu Pro Glu Gln Val Asp Ala Ile Val Ser Glu
                85                  90                  95

Trp Met Gly Tyr Gly Leu Leu His Glu Ser Met Leu Ser Ser Val Leu
            100                 105                 110

His Ala Arg Thr Lys Trp Leu Lys Glu Gly Gly Leu Leu Leu Pro Ala
        115                 120                 125

Ser Ala Glu Leu Phe Ile Ala Pro Ile Ser Asp Gln Met Leu Glu Trp
    130                 135                 140

Arg Leu Gly Phe Trp Ser Gln Val Lys Gln His Tyr Gly Val Asp Met
145                 150                 155                 160

Ser Cys Leu Glu Gly Phe Ala Thr Arg Cys Leu Met Gly His Ser Glu
                165                 170                 175

Ile Val Val Gln Gly Leu Ser Gly Glu Asp Val Leu Ala Arg Pro Gln
            180                 185                 190

Arg Phe Ala Gln Leu Glu Leu Ser Arg Ala Gly Leu Glu Gln Glu Leu
        195                 200                 205

Glu Ala Gly Val Gly Gly Arg Phe Arg Cys Ser Cys Tyr Gly Ser Ala
    210                 215                 220

Pro Met His Gly Phe Ala Ile Trp Phe Gln Val Thr Phe Pro Gly Gly
225                 230                 235                 240

Glu Ser Glu Lys Pro Leu Val Leu Ser Thr Ser Pro Phe His Pro Ala
                245                 250                 255

Thr His Trp Lys Gln Ala Leu Leu Tyr Leu Asn Glu Pro Val Gln Val
            260                 265                 270

Glu Gln Asp Thr Asp Val Ser Gly Glu Ile Thr Leu Leu Pro Ser Arg
        275                 280                 285

Asp Asn Pro Arg Arg Leu Arg Val Leu Leu Arg Tyr Lys Val Gly Asp
    290                 295                 300

Gln Glu Glu Lys Thr Lys Asp Phe Ala Met Glu Asp
305                 310                 315
```

<210> SEQ ID NO 13
<211> LENGTH: 1780
<212> TYPE: DNA
<213> ORGANISM: Homo sapiens

<400> SEQUENCE: 13

```
caccgaattc gccggatcta agatggcagc ggcggcggcg gcggtggggc cgggcgcggg      60

cggcgcgggg tcggcggtcc cgggcggcgc ggggccctgc gctaccgtgt cggtgttccc     120

cggcgcccgc ctcctcacca tcggcgacgc gaacggcgag atccagcggc acgcggagca     180

gcaggcgctg cgcctcgagg tgcgcgccgg cccggactcg gcgggcatcg ccctctacag     240
```

```
ccatgaagat gtgtgtgtct ttaagtgctc agtgtcccga gagacagagt gcagccgtgt    300

gggcaagcag tccttcatca tcaccctggg ctgcaacagc gtcctcatcc agttcgccac    360

acccaacgat ttctgttcct tctacaacat cctgaaaacc tgccggggcc acaccctgga    420

gcggtctgtg ttcagcgagc ggacggagga gtcttctgcc gtgcagtact tccagtttta    480

tggctacctg tcccagcagc agaacatgat gcaggactac gtgcggacag gcacctacca    540

gcgcgccatc ctgcaaaacc acaccgactt caaggacaag atcgttcttg atgttggctg    600

tggctctggg atcctgtcgt tttttgccgc ccaagctgga gcacggaaaa tctacgcggt    660

ggaggccagc accatggccc agcacgctga ggtcttggtg aagagtaaca acctgacgga    720

ccgcatcgtg gtcatcccgg gcaaggtgga ggaggtgtca ctccccgagc aggtggacat    780

catcatctcg gagcccatgg gctacatgct cttcaacgag cgcatgctgg agagctacct    840

ccacgccaag aagtacctga agcccagcgg aaacatgttt cctaccattg gtgacgtcca    900

ccttgcaccc ttcacggatg aacagctcta catggagcag ttcaccaagg ccaacttctg    960

gtaccagcca tctttccatg gagtggacct gtcggccctc cgaggtgccg cggtggatga   1020

gtatttccgg cagcctgtgg tggacacatt tgacatccgg atcctgatgg ccaagtctgt   1080

caagtacacg gtgaacttct tagaagccaa agaaggagat ttgcacagga tagaaatccc   1140

attcaaattc cacatgctgc attcagggct ggtccacggc ctggctttct ggtttgacgt   1200

tgctttcatc ggctccataa tgaccgtgtg gctgtccaca gccccgacag agcccctgac   1260

ccactggtac caggtgcggt gcctgttcca gtcaccactg ttcgccaagg caggggacac   1320

gctctcaggg acatgtctgc ttattgccaa caaaagacag agctacgaca tcagtattgt   1380

ggcccaggtg gaccagaccg gctccaagtc cagtaacctc ctggatctga aaaacccctt   1440

ctttagatac acgggcacaa cgccctcacc cccacccggc tcccactaca catctccctc   1500

ggaaaacatg tggaacacgg gcagcaccta caacctcagc agcgggatgg ccgtggcagg   1560

gatgccgacc gcctatgact tgagcagtgt tattgccagt ggctccagcg tgggccacaa   1620

caacctgatt cctttagggt cctccggcgc ccagggcagt ggtggtggca gcacgagtgc   1680

ccactatgca gtcaacagcc agttcaccat gggcggcccc gccatctcca tggcgtcgcc   1740

catgtccatc ccgaccaaca ccatgcacta cgggagctag                          1780
```

<210> SEQ ID NO 14
<211> LENGTH: 1849
<212> TYPE: DNA
<213> ORGANISM: Homo sapiens

<400> SEQUENCE: 14

```
caccgaattc gccggatcta agatggcagc ggcggcggcg gcggtggggc cgggcgcggg     60

cggcgcgggg tcggcggtcc cgggcggcgc ggggccctgc gctaccgtgt cggtgttccc    120

cggcgcccgc ctcctcacca tcggcgacgc gaacggcgag atccagcggc acgcggagca    180

gcaggcgctg cgcctcgagg tgcgcgccgg cccggactcg gcgggcatcg ccctctacag    240

ccatgaagat gtgtgtgtct ttaagtgctc agtgtcccga gagacagagt gcagccgtgt    300

gggcaagcag tccttcatca tcaccctggg ctgcaacagc gtcctcatcc agttcgccac    360

acccaacgat ttctgttcct tctacaacat cctgaaaacc tgccggggcc acaccctgga    420

gcggtctgtg ttcagcgagc cgacggagga gtcttctgcc gtgcagtact tccagtttta    480

tggctacctg tcccagcagc agaacatgat gcaggactac gtgcggacag gcacctacca    540
```

-continued

```
gcgcgccatc ctgcaaaacc acaccgactt caaggacaag atcgttcttg atgttggctg    600

tggctctggg atcctgtcgt tttttgccgc ccaagctgga gcacggaaaa tctacgcggt    660

ggaggccagc accatggccc agcacgctga ggtcttggtg aagagtaaca acctgacgga    720

ccgcatcgtg gtcatcccgg gcaaggtgga ggaggtgtca ctccccgagc aggtggacat    780

catcatctcg gagcccatgg gctacatgct cttcaacgag cgcatgctgg agagctacct    840

ccacgccaag aagtacctga agcccagcgg aaacatgttt cctaccattg gtgacgtcca    900

ccttgcaccc ttcacggatg aacagctcta catggagcag ttcaccaagg ccaacttctg    960

gtaccagcca tctttccatg gagtggacct gtcggccctc cgaggtgccg cggtggatga   1020

gtatttccgg cagcctgtgg tggacacatt tgacatccgg atcctgatgg ccaagtctgt   1080

caagtacacg gtgaacttct tagaagccaa agaaggagat ttgcacagga tagaaatccc   1140

attcaaattc cacatgctgc attcagggct ggtccacggc ctggctttct ggtttgacgt   1200

tgctttcatc ggctccataa tgaccgtgtg gctgtccaca gccccgacag agcccctgac   1260

ccactggtac caggtgcggt gcctgttcca gtcaccactg ttcgccaagg caggggacac   1320

gctctcaggg acatgtctgc ttattgccaa caaaagacag agctacgaca tcagtattgt   1380

ggcccaggtg gaccagaccg gctccaagtc cagtaacctc ctggatctga aaaacccctt   1440

ctttagatac acgggcacaa cgccctcacc cccacccggc tcccactaca catctccctc   1500

ggaaaacatg tggaacacgg gcagcaccta caacctcagc agcgggatgg ccgtggcagg   1560

gatgccgacc gcctatgact tgagcagtgt tattgccagt ggctccagcg tgggccacaa   1620

caacctgatt cctttagcca acacggggat tgtcaatcac acccactccc ggatgggctc   1680

cataatgagc acggggattg tccaagggtc ctccggcgcc cagggcagtg gtggtggcag   1740

cacgagtgcc cactatgcag tcaacagcca gttcaccatg ggcggccccg ccatctccat   1800

ggcgtcgccc atgtccatcc cgaccaacac catgcactac gggagctag               1849
```

<210> SEQ ID NO 15
<211> LENGTH: 585
<212> TYPE: PRT
<213> ORGANISM: Homo sapiens

<400> SEQUENCE: 15

```
Met Ala Ala Ala Ala Ala Ala Val Gly Pro Gly Ala Gly Gly Ala Gly
1               5                   10                  15

Ser Ala Val Pro Gly Gly Ala Gly Pro Cys Ala Thr Val Ser Val Phe
            20                  25                  30

Pro Gly Ala Arg Leu Leu Thr Ile Gly Asp Ala Asn Gly Glu Ile Gln
        35                  40                  45

Arg His Ala Glu Gln Gln Ala Leu Arg Leu Glu Val Arg Ala Gly Pro
    50                  55                  60

Asp Ser Ala Gly Ile Ala Leu Tyr Ser His Glu Asp Val Cys Val Phe
65                  70                  75                  80

Lys Cys Ser Val Ser Arg Glu Thr Glu Cys Ser Arg Val Gly Lys Gln
                85                  90                  95

Ser Phe Ile Ile Thr Leu Gly Cys Asn Ser Val Leu Ile Gln Phe Ala
            100                 105                 110

Thr Pro Asn Asp Phe Cys Ser Phe Tyr Asn Ile Leu Lys Thr Cys Arg
        115                 120                 125

Gly His Thr Leu Glu Arg Ser Val Phe Ser Glu Arg Thr Glu Glu Ser
    130                 135                 140
```

-continued

```
Ser Ala Val Gln Tyr Phe Gln Phe Tyr Gly Tyr Leu Ser Gln Gln Gln
145                 150                 155                 160

Asn Met Met Gln Asp Tyr Val Arg Thr Gly Thr Tyr Gln Arg Ala Ile
                165                 170                 175

Leu Gln Asn His Thr Asp Phe Lys Asp Lys Ile Val Leu Asp Val Gly
            180                 185                 190

Cys Gly Ser Gly Ile Leu Ser Phe Phe Ala Ala Gln Ala Gly Ala Arg
        195                 200                 205

Lys Ile Tyr Ala Val Glu Ala Ser Thr Met Ala Gln His Ala Glu Val
    210                 215                 220

Leu Val Lys Ser Asn Asn Leu Thr Asp Arg Ile Val Val Ile Pro Gly
225                 230                 235                 240

Lys Val Glu Glu Val Ser Leu Pro Glu Gln Val Asp Ile Ile Ile Ser
                245                 250                 255

Glu Pro Met Gly Tyr Met Leu Phe Asn Glu Arg Met Leu Glu Ser Tyr
            260                 265                 270

Leu His Ala Lys Lys Tyr Leu Lys Pro Ser Gly Asn Met Phe Pro Thr
        275                 280                 285

Ile Gly Asp Val His Leu Ala Pro Phe Thr Asp Glu Gln Leu Tyr Met
    290                 295                 300

Glu Gln Phe Thr Lys Ala Asn Phe Trp Tyr Gln Pro Ser Phe His Gly
305                 310                 315                 320

Val Asp Leu Ser Ala Leu Arg Gly Ala Ala Val Asp Glu Tyr Phe Arg
                325                 330                 335

Gln Pro Val Val Asp Thr Phe Asp Ile Arg Ile Leu Met Ala Lys Ser
            340                 345                 350

Val Lys Tyr Thr Val Asn Phe Leu Glu Ala Lys Glu Gly Asp Leu His
        355                 360                 365

Arg Ile Glu Ile Pro Phe Lys Phe His Met Leu His Ser Gly Leu Val
    370                 375                 380

His Gly Leu Ala Phe Trp Phe Asp Val Ala Phe Ile Gly Ser Ile Met
385                 390                 395                 400

Thr Val Trp Leu Ser Thr Ala Pro Thr Glu Pro Leu Thr His Trp Tyr
                405                 410                 415

Gln Val Arg Cys Leu Phe Gln Ser Pro Leu Phe Ala Lys Ala Gly Asp
            420                 425                 430

Thr Leu Ser Gly Thr Cys Leu Leu Ile Ala Asn Lys Arg Gln Ser Tyr
        435                 440                 445

Asp Ile Ser Ile Val Ala Gln Val Asp Gln Thr Gly Ser Lys Ser Ser
    450                 455                 460

Asn Leu Leu Asp Leu Lys Asn Pro Phe Phe Arg Tyr Thr Gly Thr Thr
465                 470                 475                 480

Pro Ser Pro Pro Pro Gly Ser His Tyr Thr Ser Pro Ser Glu Asn Met
                485                 490                 495

Trp Asn Thr Gly Ser Thr Tyr Asn Leu Ser Ser Gly Met Ala Val Ala
            500                 505                 510

Gly Met Pro Thr Ala Tyr Asp Leu Ser Ser Val Ile Ala Ser Gly Ser
        515                 520                 525

Ser Val Gly His Asn Asn Leu Ile Pro Leu Gly Ser Ser Gly Ala Gln
    530                 535                 540

Gly Ser Gly Gly Gly Ser Thr Ser Ala His Tyr Ala Val Asn Ser Gln
545                 550                 555                 560

Phe Thr Met Gly Gly Pro Ala Ile Ser Met Ala Ser Pro Met Ser Ile
```

-continued

```
                565                 570                 575

Pro Thr Asn Thr Met His Tyr Gly Ser
            580                 585
```